US005491411A

United States Patent [19]
Wellstood et al.

[11] Patent Number: 5,491,411
[45] Date of Patent: Feb. 13, 1996

[54] METHOD AND APPARATUS FOR IMAGING MICROSCOPIC SPATIAL VARIATIONS IN SMALL CURRENTS AND MAGNETIC FIELDS

[75] Inventors: Frederick C. Wellstood, College Park; Anna Mathai, University Park; Dian Song, Greenbelt; Randall C. Black, Seabrook, all of Md.

[73] Assignee: University of Maryland, College Park, Md.

[21] Appl. No.: 61,102

[22] Filed: May 14, 1993

[51] Int. Cl.$^6$ .................. G01R 33/035; G01R 33/12; G01N 27/72
[52] U.S. Cl. .................. 324/248; 324/201; 324/224; 324/235; 324/239; 324/262; 505/162; 505/846
[58] Field of Search ................... 324/201, 224, 324/226, 229, 235, 239–243, 248, 262; 505/162, 846

[56] References Cited

U.S. PATENT DOCUMENTS

| | | |
|---|---|---|
| 3,454,875 | 7/1969 | Bol et al. . |
| 4,004,217 | 1/1977 | Giffard . |
| 4,465,975 | 8/1984 | Porter . |
| 4,492,923 | 1/1985 | Bryam . |
| 4,588,947 | 5/1986 | Ketchen . |
| 4,591,787 | 5/1986 | Hoenig . |
| 4,613,816 | 9/1986 | Zeamer . |
| 4,613,817 | 9/1986 | Hoenig . |
| 4,771,239 | 9/1988 | Hoenig . |
| 4,801,882 | 1/1989 | Daalmans .................. 324/248 |
| 4,987,367 | 1/1991 | Ishikawa et al. .................. 324/248 X |
| 5,053,706 | 10/1991 | Ohkawa . |
| 5,103,682 | 4/1992 | Moreland . |
| 5,134,368 | 7/1992 | Otaka et al. .................. 324/248 X |
| 5,184,072 | 2/1993 | Yuyama et al. .................. 324/248 |
| 5,248,941 | 9/1993 | Lee et al. .................. 324/248 |
| 5,293,119 | 3/1994 | Podney .................. 324/262 X |

FOREIGN PATENT DOCUMENTS 4-2979   1/1992   Japan .................. 324/248

OTHER PUBLICATIONS

Nave et al; Micromagnetic Susceptometer; Rev. Sci. Instrum. 51(5) May 1980, pp. 591–596.
Pelizzone et al; A SQUID Susceptometer for Fields up to 8.5 Tesla; Appl. Phys. 24, No. 4, Apr. 1984, pp. 375–379.
"On Inhomogeneities in the Magnetization of Ferromagnetic Materials," Phys. Rev. vol. 38, pp. 1903–1905, Nov. 1931, authored by F. Bitter.
"The Structure of the Superconductors in the Intermediate State," J. Phys., vol. 9, pp. 202–210, Jun. 1945, authored by A. Shalnikov.
"Scanning Hall Probe Microscopy of a Vortex Field and Fluctuations in $La_{1.85}Sr_{0.15}CuO_4$", authored by A. M. Chang et al., submitted to Phys. Rev. Lett.
"Observation of Magnetic Domains by the Kerr Effect," Phys. Rev., vol. 82, pp. 119–120, Apr. 1951 authored by H. J. Williams et al.
"Magnetic Imaging by Force Microscopy with 1000 A Resolution," Appl. Phys. Lett., vol. 50, pp. 1455–1457, May 1987 authored by Y. Martin et al.
"Magnetic Field Observation of a Single Flux Quantum by Electron–Holographic Interferometry," Phys. Rev. Lett., vol. 62, pp. 2519–2522, May 1989, authored by T. Matsuda et al.
"Microsquid: A Close Spaced Four Channel Magnetometer", *Advances in Biomagnetism*, Plenum, New York: S. J. Williamson, 1989, pp. 677–679, authored by D. S. Buchanan et al.

(List continued on next page.)

*Primary Examiner*—Gerard R. Strecker
*Attorney, Agent, or Firm*—Fisher & Associates

[57] ABSTRACT

A magnetic flux microscope that measures the magnetic field about a sample surface. The apparatus uses a thin-film superconducting quantum interference device (SQUID) as the scanning device. Magnetic shielding is provided about the SQUID and is held stationary relative to the SQUID. The apparatus and method provides a very high magnetic image of the sample with a very high spatial and field resolution.

24 Claims, 30 Drawing Sheets

OTHER PUBLICATIONS

"Gas Floating Technique for Detection of Trapped Flux Quanta." Physics B, vol. 165, pp. 87–88, Aug. 1990 authored by Q. Geng et al.

"A Single–Chip SQUID Magnetometer," IEEE Transactions on Electron Devices., vol. 35, No. 12, Dec. 1988 authored by N. Fujimaki et al.

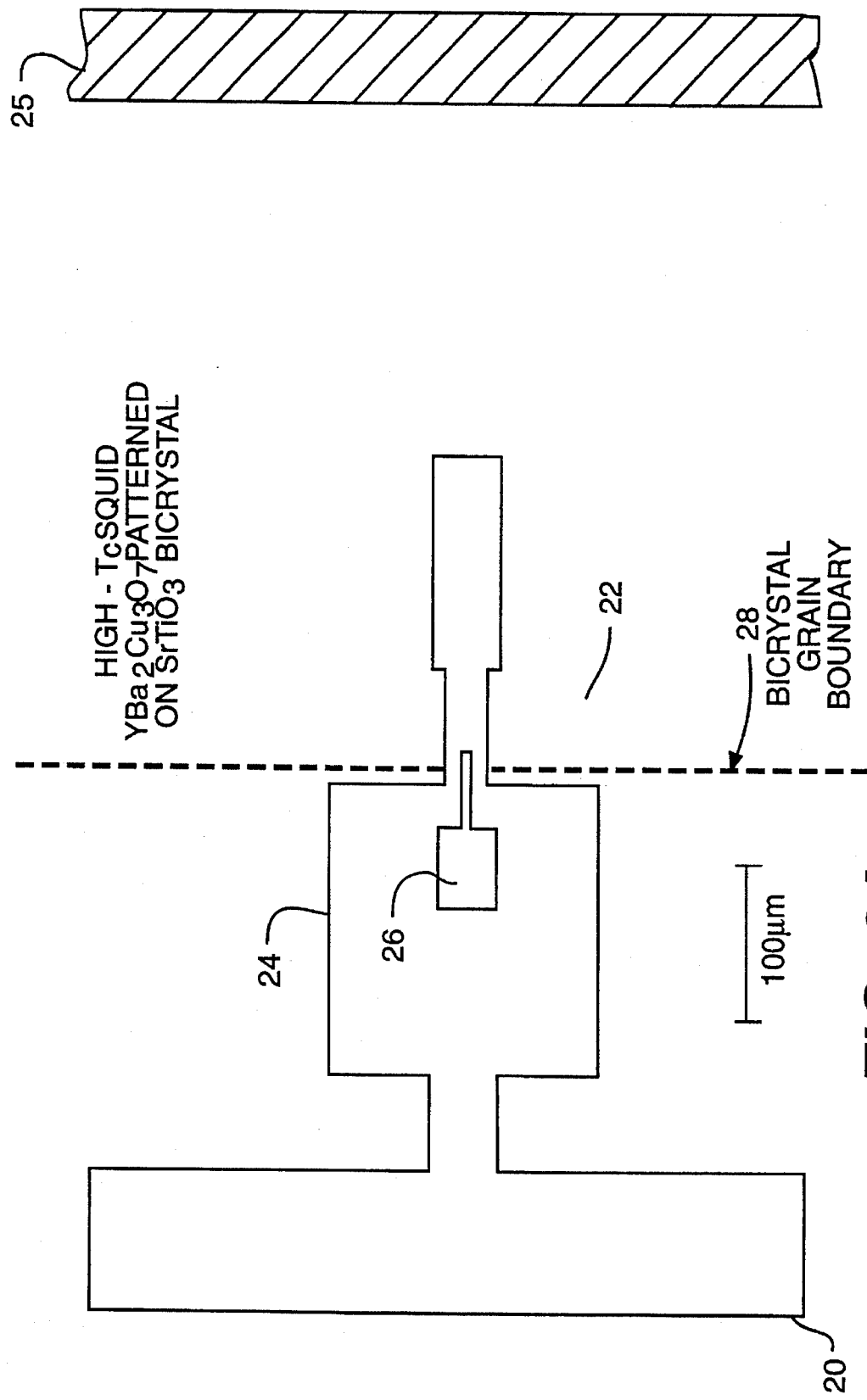

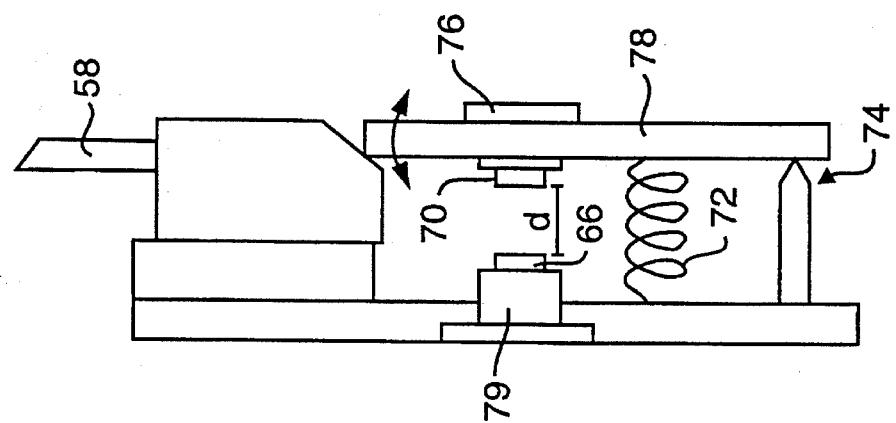
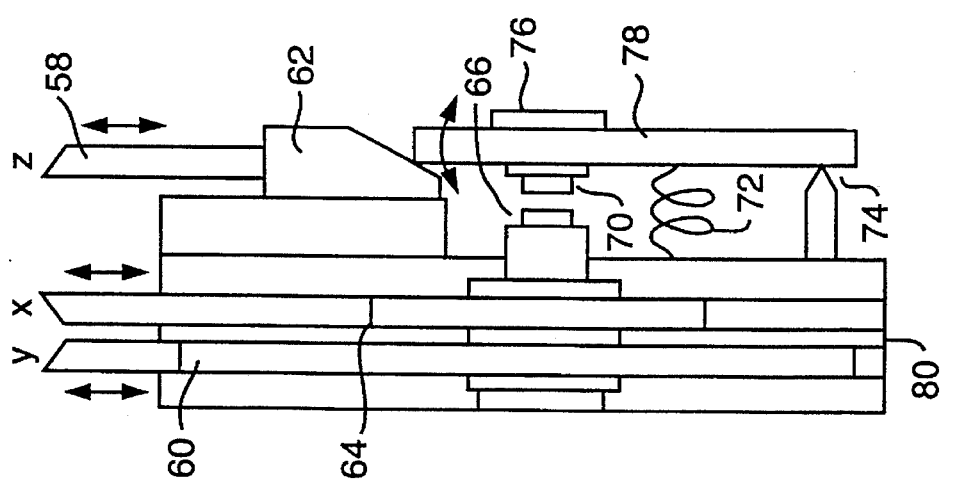
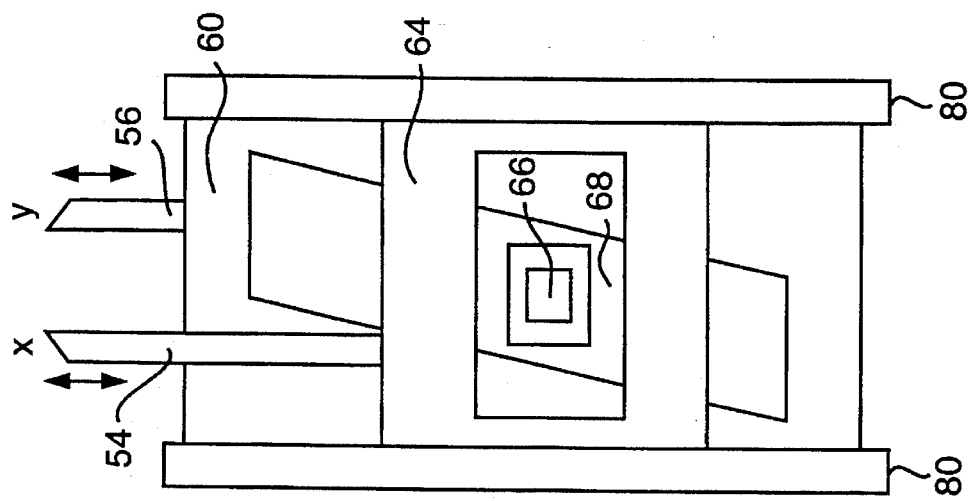

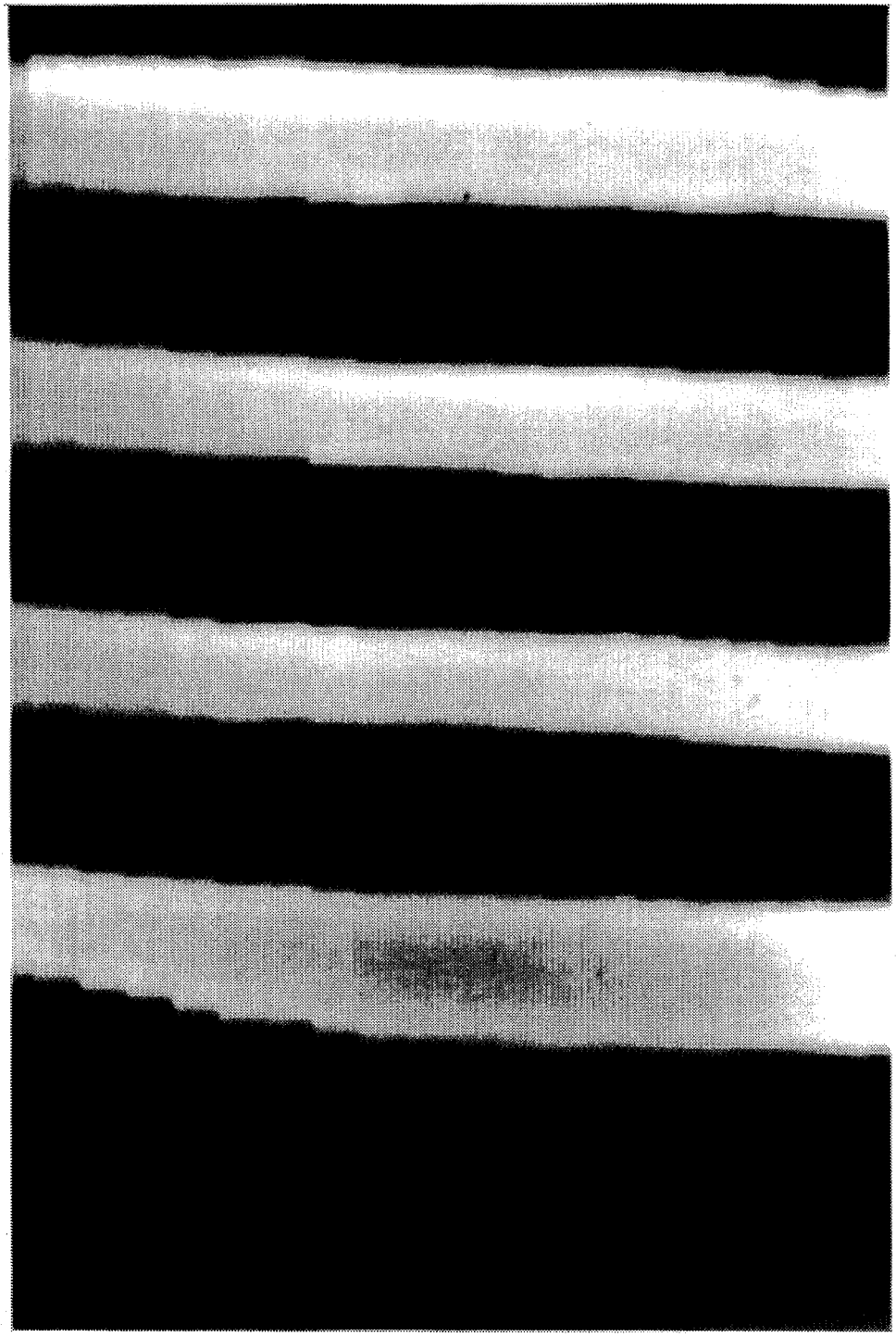

METHOD AND APPARATUS FOR IMAGING MICROSCOPIC SPATIAL VARIATIONS IN SMALL CURRENTS AND MAGNETIC FIELDS

BACKGROUND OF THE INVENTION

The invention relates to magnetic field measuring devices, and more specifically, to magnetic flux microscopes used to produce microscopic magnetic images of samples.

A number of techniques have been developed to image magnetic fields at length scales of a few µm or relatively smaller. These include decoration techniques, magnetoresistive or Hall probe sensors, magneto-optic thin films, magnetic force microscopy, and electron beam interferometry. These have provided limited success and are not practical for high resolution and high sensitivity imaging of fields and flux lines.

Examples of the above techniques are disclosed in the following articles:

"On Inhomogeneities in the Magnetization of Ferromagnetic Materials," Phys. Rev. vol. 38, pp 1903–1905, November 1931 authored by F. Bitter.

"The Structure of the Superconductors in the Intermediate State," J. Phys., vol. 9, pp. 202–210, June 1945 authored by A. Shalnikov.

"Scanning Hall Probe Microscopy of a Vortex Field Fluctuations in $La_{1.85}Sr_{0.15}CuO_4$" authored by A. M. Chang et al., submitted to Phys. Rev. Lett.

"Observation of Magnetic Domains by the Kerr effect," Phys. Rev., vol. 82, pp. 119–120, April 1951 authored by H. J Williams et al.

"Force Microscopy with 1000 A Resolution." Appl. Phys. Lett., vol. 50, pp. 1455–1457, May 1987 authored by Y. Martin et al.

"Magnetic Field Observation of a Single Flux Quantum by Electron-Holographic Interferometry," Phys. Rev. Lett., vol. 62, pp. 2519–2522, May 1989, authored by T. Matsuda et al.

Additionally, a number of susceptometers and magnetometers have been proposed using Superconducting Quantum Interference Devices or SQUIDs. Though previous SQUID systems have been developed to provide high magnetic field resolution they are impractical to implement in an imaging microscope device. The prior art magnetic imaging devices using SQUIDs have relied on the scale of a mm or larger. See for example:

*Advances in Biomagnetism*, Plenum, New York.: S. J. Williamson, 1989, pp.677–679, authored by D. S. Buchanan et al.

"Gas Floating Technique for Detection of Trapped Flux Quanta." Physics B, vol. 165, pp. 87–88, August 1990 authored by Q. Geng et al.

"A Single-Chip SQUID Magnetometer," IEEE Transactions on Electron Dev., vol 35, No. 12, Dec. 1988 authored by N. Fujimaki et al.

This scale does not provide the resolution required for problems in the manufacturing, microelectronic and magnetic media industries. Moreover, many of the prior art devices and methods are cost intensive to manufacture and implement. Examples of these include various embodiments as shown in U.S. Pat. Nos. 4,801,882 (Daalmans); 4,771,239 (Hoenig); 4,613,817 (Hoenig); 4,591,787 (Hoenig); 4,588,947 (Ketchen); 4,492,923 (Bryam) and 4,613,816 (Zeamer).

In recent years, since the advent of the high transition temperature ($T_c$) superconductors and related advances in superconductor technology, many industries have found a greater need to measure superconductor characteristics of materials. The process of magnetic imaging at high resolution and high sensitivity of fields in materials has been impractical while low sensitivity measurements have been lengthy or expensive. This has slowed the hopeful discovery of room temperature superconductors and new high temperature superconductors.

In the field of semiconductor/microelectronics testing, there is a need to measure the current flow and image the data relating the operation of semiconductor/microelectronic devices and the related current paths. The devices currently used have proved to be of limited use in these endeavors because they cannot image the flow of small currents in microelectronic structures. These semiconductor testing devices have utilized both non-destructive testing and destructive testing.

With the advent of magnetic resonance imaging in the field of biology, many new discoveries have been made regarding biological and biochemical subjects. Unfortunately, none of the current technologies applied in this field can provide a very sensitive reading in the picotesla range. A high resolution and highly sensitive magnetic flux microscope using SQUID technology is needed in many fields of biology, ceramics, metallurgy, magnetic media, physics, microelectronics and many other fields.

SUMMARY OF THE INVENTION

It is therefore an object of the invention to provide a magnetic flux microscope with a high spatial and magnetic field resolution.

It is a further object of the invention to provide a microscopic spatial representation of the magnetic characteristics of a sample which is free from the effect of noise and stray fields.

It is yet another object of the invention to provide a non-destructive testing device for samples.

It is yet another object of the invention to provide an aid to examining biologic and biochemical matter.

It is yet another object of the invention to provide a device for imaging the flow of electrical currents in microelectronic circuits, printed circuit boards, and other electrical devices and structures.

In all of the above embodiments, it is an object of the present invention to provide a simple and cost effective manner to test electrical and magnetic characteristics of samples.

The present invention is a highly sensitive magnetic microscope which uses a bare dc SQUID as a magnetic sensor. In one implementation of this invention, the magnetic sensor is a High Tc dc SQUID as shown in FIG. 2. The SQUID is made from a thin-film of a high-temperature superconductor, such as $YBa_2Cu_3O_7$, that is deposited on a chip, which may be made of $SrTiO_3$. The SQUID loop is designed to be very small so as to allow the microscope to resolve very small spatial features. A center hole is provided and is preferably 50 µm in diameter. This SQUID, as fabricated, may discern magnetic features as small as 20 picoTesla with a one second averaging time. The microscope may image an area of about 1 $cm^2$ and resolve features down to approximately 50 µm.

SQUID and a sample are movable relative to each other in three orthogonal axes, i.e., x, y, and z, to allow for three dimensional scanning of the sample as shown in FIGS. 4A and 4B. The SQUID is preferably movable in the Z-direction and the sample in the X and Y directions. The SQUID and sample are enclosed in two magnetic shields and submerged in a dewar of liquid nitrogen, or other such coolant, as shown in FIG. 5A. Two additional magnetic shields are placed around dewar and the entire system is placed in a magnetically shielded room (not shown).

The voltage across the SQUID is sensed as a function of the position of the sample to provide analog outputs that are converted into digital signals through an A/D board, as shown in FIG. 6. Data is then processed by a computer imaging system to provide a 1D, 2D or 3D representation of the magnetic characteristics of the sample.

Other objects and features of the present invention will be apparent from the following detailed description of the preferred embodiment.

BRIEF DESCRIPTION OF THE DRAWINGS

The invention will be further described in conjunction with the accompanying drawings, in which:

FIG. 2A is a block diagram of the high-Tc SQUID used in a (3-D) scanner;

FIG. 2B is a block diagram of the high-Tc SQUID relative to the field coil;

FIG. 4A is a front elevational view of sample stage and positioning assembly for 3-D magnetic flux microscope;

FIG. 4B is a side elevational view of sample stage and positioning assemble for the 3-D magnetic flux microscope of FIG. 4A;

FIG. 4C is a side elevational view of the sample stage showing the distance between the sample and the SQUID.

FIG. 7B illustrates the magnetic image of the wire sample with an applied current of 800 mA;

DETAILED DESCRIPTION OF THE INVENTION

The present invention discloses the design, construction and application of magnetic microscopes which are based on thin-film Superconducting Quantum Interference Devices (SQUIDs).

There are several important design considerations for a SQUID-based magnetic microscope. First, to achieve the best possible spatial resolution, it is essential to use a small SQUID and scan it as close as possible to the sample. For micron-scale resolution, this necessitates placing both SQUID and sample together in a cryogenic dewar. Next, one should be able to scan the sample in at least two dimensions and adjust the separation between the sample and the SQUID. The necessary positioning mechanism must not

1-D MICROSCOPE

Figure 1:
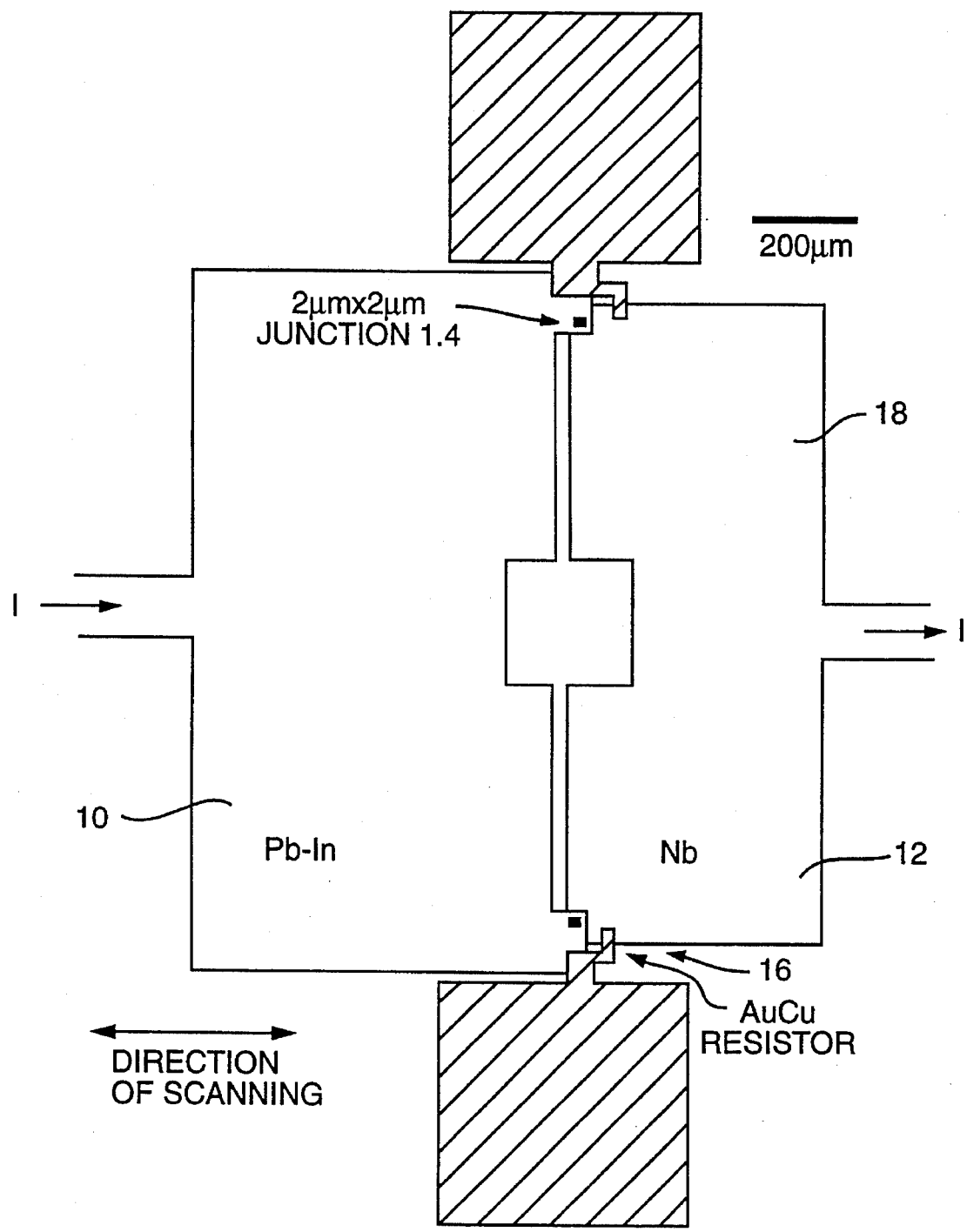
FIG. 1 is a block diagram of the low-Tc SQUID used in a 1-dimensional (1-D) scanner.

The low-$T_c$ SQUID as shown in FIG. 1 is a thin-film-washer dc SQUID which is preferably made from Nb 12 and Pb(5 wt %In) 10. The device is preferably made on a 5 mm² chip of silicone Si 18 and has an outer size of about 1 mm, an inner hole size of 200 µm, and an effective magnetic field pick-up area of 0.28 mm². Electrical connections to the SQUID are made by pressing contacts onto thin-film pads deposited onto the opposite side of the Si chip 18. The junction 14 is approximately 2 µm×2 µm. A AuCu resistor 16 is formed to connect the Pb-In 10 and Nb 12 electrodes of the junctions 14.

Figure 3A:
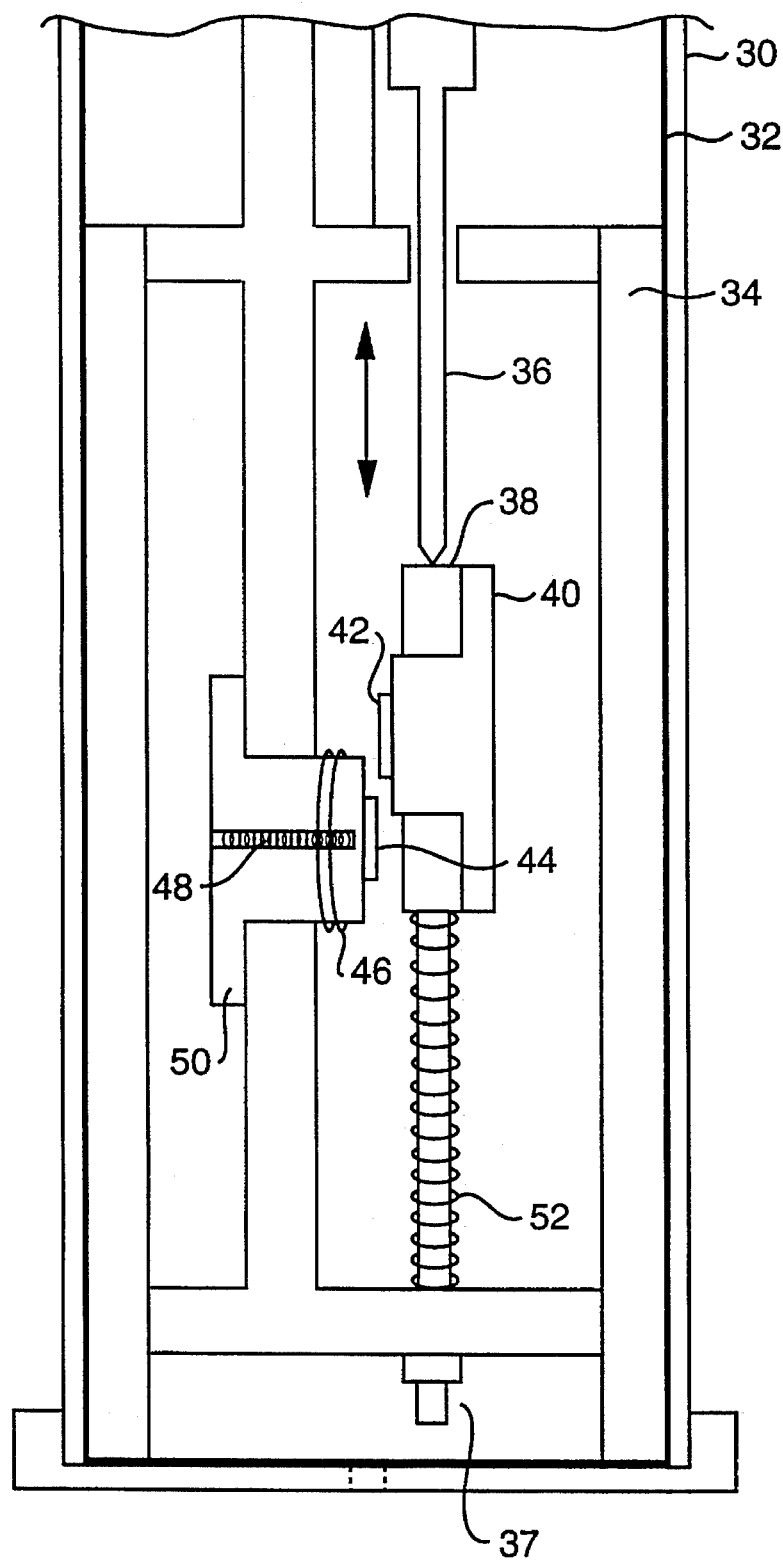
FIG. 3A is a diagram of the cryogenic portion of the 1D magnetic flux microscope assembly constructed in accordance with a preferred embodiment of the invention.
Figure 3B:
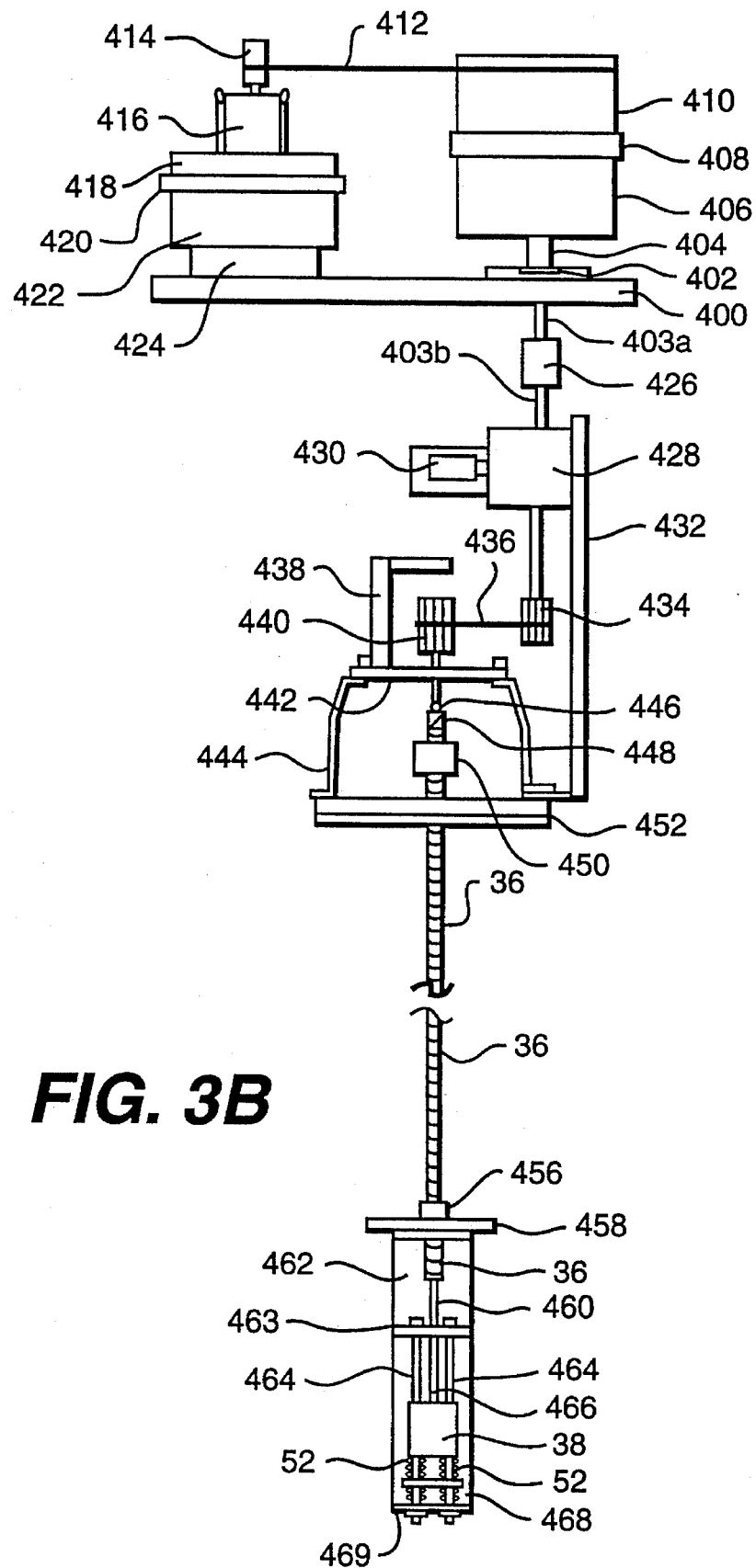
FIG. 3B is a detailed schematic of the sample positioner drive assembly for the 1-D magnetic microscope of FIG. 3A.
Figure 6:
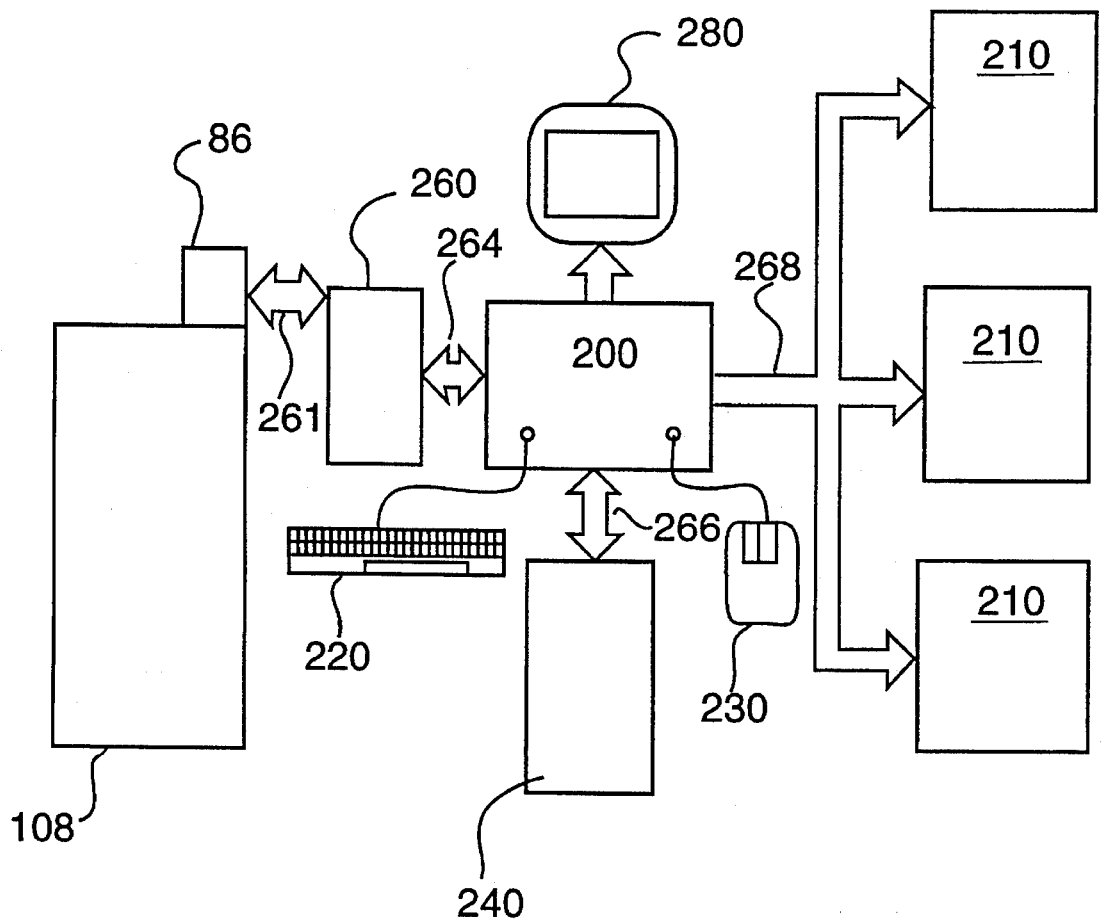
FIG. 6 is block diagram of a magnetic flux microscope system constructed in accordance with a preferred embodiment of the invention.

The cryogenic assembly of the 1-D microscope is shown in FIG. 3A. The sample 42 is affixed to a Delrin™ sample holder 40 which is attached to a slider 38. The slider 38 rides on a pair of brass rods 464 (see FIG. 3B) and 37 and is held against a push rod 36 by Cu-Be springs 52. The separation between sample 42 and SQUID 44 is adjusted at room temperature. During a scan, a computer 200 as shown in FIG. 6, controls a stepper motor 416 turning room temperature drive screws 446 to advance push rod 36, thereby moving slider 38 and sample 42 past SQUID 44 as shown in FIG. 3B. Motor 416 is coupled to drive screw 446 through a drive belt system 412 and 436, a vibration isolator assembly 406, 410, 418, 422 and a gear arrangement 426, 428, 432, 434, 438, 440. The sample position is monitored by using the above gear arrangement to step down the rotation of drive shaft 403A and 403B and turn a precision 10-turn linear potentiometer 430. The resistance of potentiometer 430 serves as a monitor of the sample position. A typical scan speed is about 8 µm/sec.

Drive screw 446 is coupled to main push rod 36 which in turn pushes sample slider 38. A superconducting field coil 46 with a heater switch 802 (see FIG. 3G) is mounted on SQUID holder 50. Typically, the mutual inductance between SQUID 44 and field coil 46, $M_a$, is 38 pH in the absence of screening. SQUID 44 is attached to a fiberglass SQUID holder 50 which is attached to a fiberglass frame 34. A feed-back coil 48 is also mounted on SQUID holder 50. The entire cryogenic positioner assembly, with sample and SQUID is then enclosed in a Pb shield 32 and immersed in liquid helium inside of dewar 112 (see FIGS. 3D and 5A).

Figure 3C:
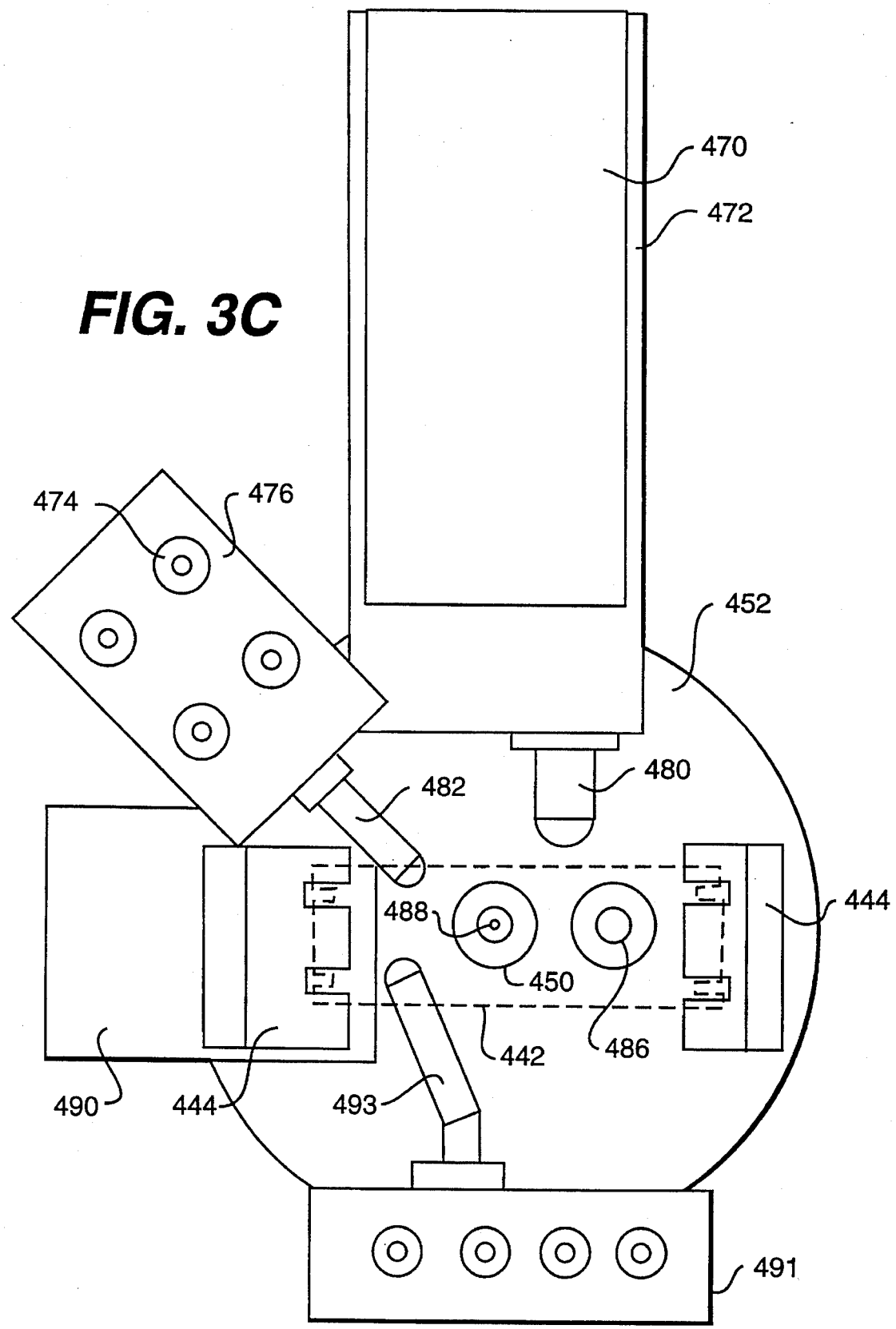
FIG. 3C is a top view of the 1-D magnetic microscope of FIG. 3A.
Figures 3D, 3E:
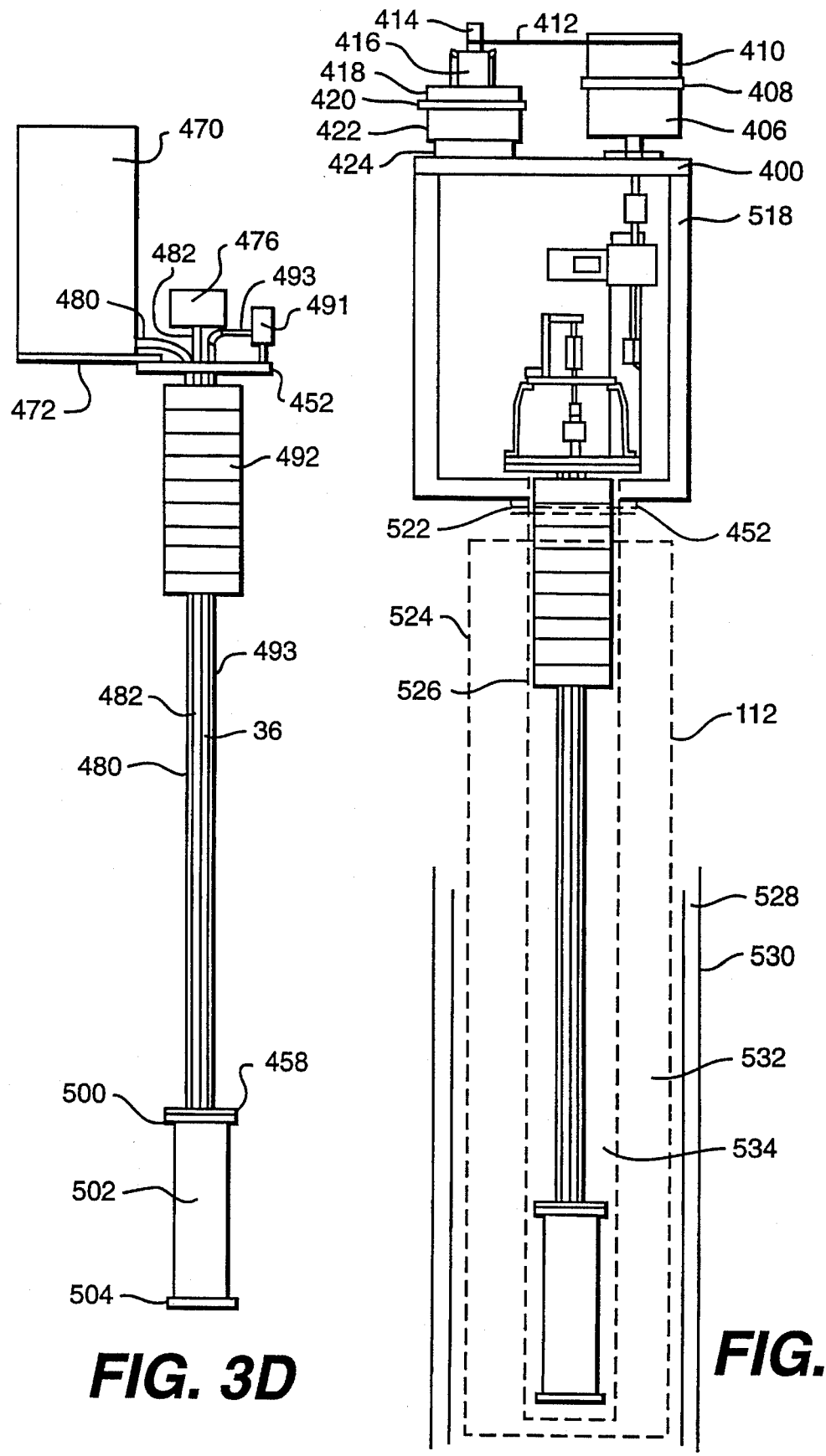
FIG. 3D is a front elevational view of the 1-D magnetic microscope of FIGS. 3A, 3B and 3C which shows the layout of the electronics boxes, having drive assembly removed for clarity.
FIG. 3E is a side view of the 1-D microscope of FIG. 3 which shows the layout of the drive mechanism, the dewar, and the magnetic shields, having the electronics and wiring tubes removed for clarity.

During imaging, SQUID 44 is maintained in a flux-locked loop by means of room temperature electronics 470, as shown in FIGS. 3C and 3D, which applies feedback flux to SQUID 44 via the feedback coil 48. It should be appreciated that the output of the electronics 470, $V_{out}$, depends on sample 42 position and the applied flux as follows:

$$V_{out} = R_f(I_a M_a + \phi_x - n\phi_0)/M_f$$

where $R_f$ is the feedback monitoring resistance and is preferably 5kΩ, $I_a$, is the current applied to field coil 48, $M_f$ and $M_a$ are, respectively, SQUID 44 feedback coil 48 mutual inductance and SQUID 44 to field coil 46 mutual inductance, and $\phi_x$ is the flux due to the sample and external field sources. In a preferred embodiment, the flux quantum is $\phi_o$ which equals 2.07×10−15 Tm² and n in an integer. The value of n is determined by the flux coupled into SQUID 44 at the moment when the feedback loop is closed; in the present invention's electronics, n is selected so that $V_{out}$ is as close to zero as possible when the loop is closed. For samples with superconducting regions, $M_f$ and $M_a$ may vary with position because of sample magnetic susceptibility or screening currents, and $\phi_x$ may vary because of trapped flux or sample magnetization.

FIG. 3B shows a detailed schematic of the sample positioning drive assembly for the 1-D magnetic microscope. For clarity, SQUID monitoring electronics, wiring boxes, and wiring tubes are not shown. Motor drive and vibration assembly are designated as components 400 through 424. Stepper motor 416 turns motor pulley 414 and rubber belt 412. Rubber belt 412 drives cylindrical vibration isolation brass masses 406 and 410 which, by drive shafts 403A and 403B, turn toothed pulleys 434 and 440. This advances drive screw 446 and forces main push rod 36 downward. Sample holder or slider 38 is held against the end of main push rod 36 by spring means 52 and slides along the two brass rods 464. Foam rubber mounts 420, 424 and 408 are used to isolate mechanical vibrations from motor 416, drive shaft coupler 404, drive shaft 403A support bearing 402, and support bracket 400.

A drive shaft coupler 426 connects the output of vibration isolator assembly drive shaft 403A to input drive shaft 403B of gear assembly 428. Gear assembly 428 is a twelve to one step down gearing device. The 10 turn potentiometer shaft rotation monitor 430 is connected to the output of the 12 times reduction gear assembly 428. Gear assembly 428 is connected to a support bracket 432. Bracket 432 is connected to the top of the top flange of dewar 452 and support brackets 444 for main drive screw 446 and drive screw pulley 440. Drive shaft 403B is connected to toothed pulley 434. Toothed pulley 434 is connected to toothed pulley 440 by a toothed rubber drive belt 436. Support bracket 400 for the motor and vibration isolation assembly is held by support bracket 518 which is attached to top of dewar 452.

Drive screw 446 passes through a threaded aperture in support plate 442 connected to brackets 444. The brass end of drive screw 446 is coupled to the brass end 448 of main push rod 36. Main push rod 36 is held in a quick connect sliding vacuum fitting 450. Main push rod 36 passes through the top flange 452 of a dewar 112. The opposite end of main push rod 36 passes through a cold flange 458 into a fiberglass support housing 468 for the internal positioning assembly. A brass extension 460 is connected to the end of main push rod 36, inside the fiberglass support housing 468. Main push rod 36 is a thin walled stainless steel rod. Support housing 468, in a preferred embodiment, is made of fiberglass. It should be appreciated that support housing 468 may be made of any other non-conductive materials, e.g., Delrin™.

Fiberglass support housing 468 incorporates an internal flange support 463 to mount smooth brass rods 464. Smooth brass rods 464 pass through sample slider 38, Cu-Be return springs 52 and bottom flange support 469 which they are secured to. Sample slider 38 rides on two brass rods 464. Return springs 52 are used to hold sample slider 38 against rounded end 466 of the brass extension to main push rod 36.

FIG. 3C is a top view showing the relative layout of SQUID monitoring electronics box 470, sample wiring boxes or enclosures 476 and BNC connectors 491, SQUID wiring tube or conduit 480 and main push rod seal fitting 450. Electronics box 470 includes room temperature feedback electronics for monitoring outputs from SQUID 44. Support bracket 472 for electronics box 470 is connected to a top flange 452 of a dewar 112. Conduit 480 is for wires to and from SQUID. Metal enclosure 476 includes a number of BNC connectors 474 for providing wiring to or from the samples. Conduit 482 is provided for these wires. Metal enclosure with BNC connectors 491 is for experimental wiring to the microscope. A conduit 493 is provided for experimental wiring. BNC connectors and related metal boxes are shown collectively in FIG. 6, as part 86. BNC connectors may be connected to an A/D or D/A board 260 to provide data into or out of microscope 108. The lower portion of the gear assembly support bracket 432, denoted as 490, is attached to support plates 444 for main drive screw 446 and pulley 440. The hashed outline of support plate 444 with a threaded hole for the drive screw is shown as element 442 to exhibit relative position of components to FIG. 3B. The threaded hole in part 442, for main drive screw 446, is designated as element 488 and is directly over main push rod 36. The outer circular area 450, designates a quick connect sliding vacuum fitting which is used to seal main push rod 36. The top flange 452 of a dewar 112 is shown having a quick connection fitting 486 to provide access for filling a dewar 112 with helium or similar gas.

Now turning to FIG. 3D, showing a front view of the 1-D magnetic microscope and illustrating the layout of the electronics boxes. The drive assembly has been removed for clarity. Feedback electronics box 470 and support bracket 472, electronics wiring box 476 and wiring box 491 are mounted on the top flange 452 of dewar 112. Conduits 480, 482 and 493 carry wiring to and from the interior of a brass shielded can 502. Brass shielded can 502 has a top flange 500 and a bottom flange 504 on either end. The flange 500 is bolted to flange 458 which is soldered to support tubes 480, 482, and 493. Brass shielded can 502 contains fiberglass support 468 and sample slider 38 and related components. At the top of conduits 480, 482 and 493 and below top flange 452 of dewar 112 are placed a number of styrofoam radiation and convection shields 492 to reduce the boil-off of liquid helium.

Figure 3F:
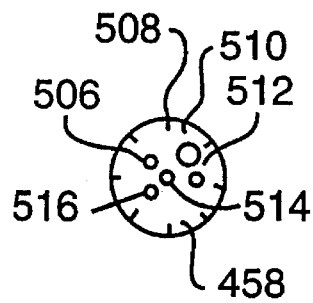
FIG. 3F is a top view of the cold flange showing the arrangement of the wiring/support tubes.

Looking at FIG. 3F, a top view of cold flange 458 may be seen. Shown are the holes for a tube for wiring sample 506; holes for tube for wiring experiments 516; holes for insertion of Teflon™ bushing 456 and main push rod 36; denoted as 514, holes for admitting of liquid helium or the like 512 into brass can 502; and holes for a tube for SQUID wiring 510. Cold flange 458 is bolted to the top of the brass shield can 502 through holes 508.

FIG. 3E, is a side view of the 1-D magnetic microscope showing the layout of the drive mechanism. Dewar 112 is a combination of elements 522, 524, 526 and 532, and magnetic shields 528 and 530. Support bracket 400 supports both motor 416 and vibration isolation assembly 518. The top flange 452 (see FIGS. 3C, 3D and 3E) of dewar 112 and a brass extension flange 522 are bolted to the bottom of support assembly 518. Through the center of this bolted assembly, conduit tubes 480, 482 and 493, and main push rod 36 pass through styrofoam radiation and convection shields 492. Dewar 112 comprises an inner wall 526 and an outer wall 524. The area between inner wall 526 and outer wall 524 comprises a vacuum space and liquid nitrogen jacket 532. The area within inner wall 526 about brass shield can 502 provides a space for liquid helium. Dewar 112 is encircled with an inner cylindrical high permeability magnetic shield 528 and an outer cylindrical high permeability magnetic shield 530 for shielding the interior of the magnetic microscope from outside electromagnetic waves and magnetic fields.

Figure 3G:
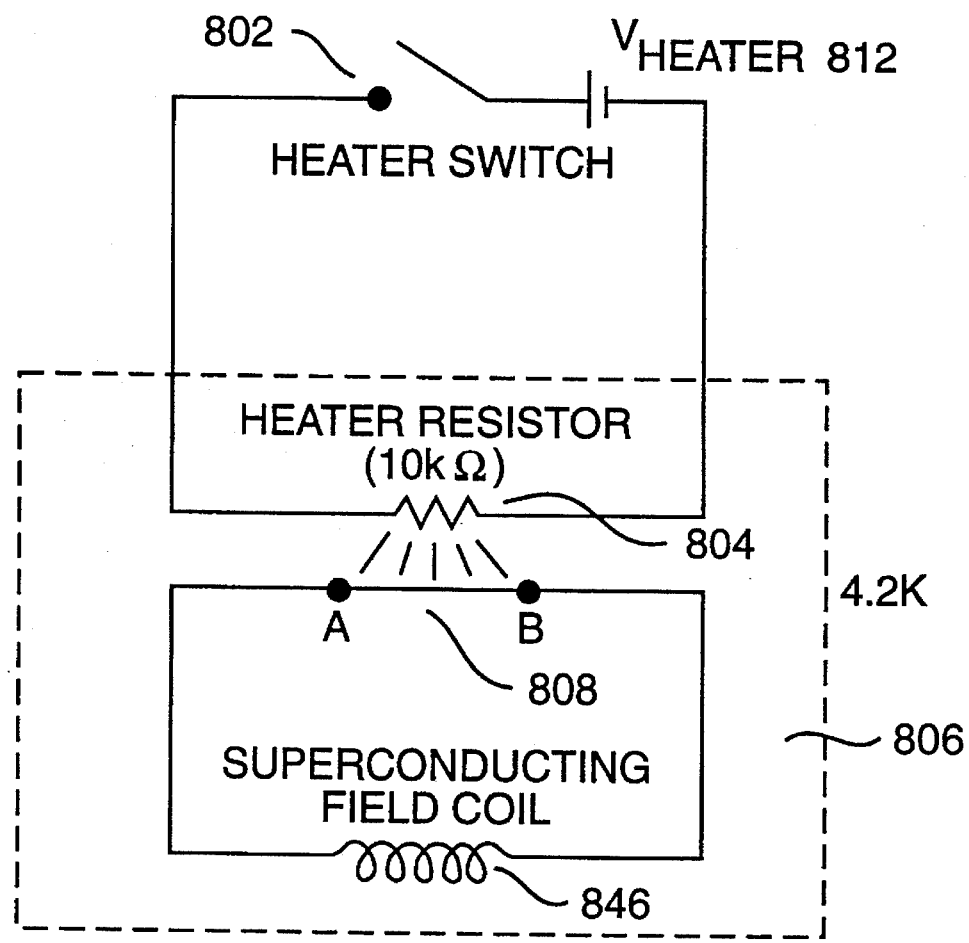
FIG. 3G is a circuit diagram of the field coil and heater switch.
Figure 3H:
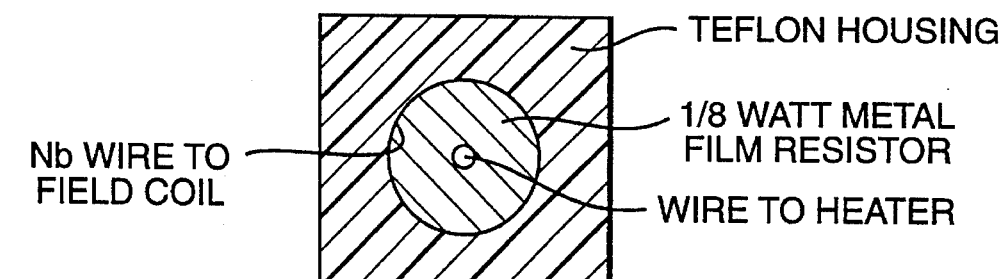
FIG. 3H is an end view of the heater switch.
Figure 3I:
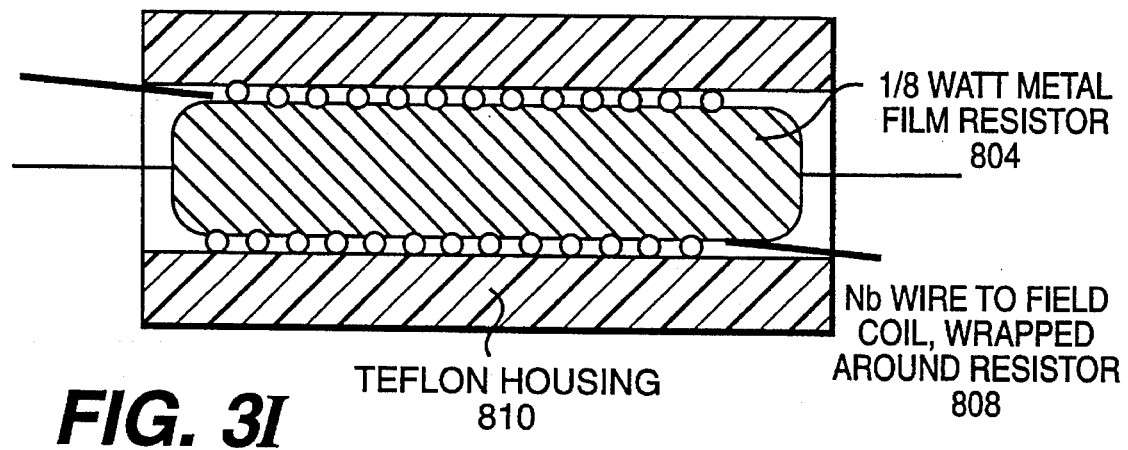
FIG. 3I is a side view of the heater resistor showing section A–B from FIG. 3G, of Nb, wire wrapped around the heater resistor.

FIG. 3G shows a circuit schematic of field coil 46, voltage supply 812, heater resistor 804 and heater switch 802. Superconducting field coil 46 is wound from Nb wire and is immersed in liquid helium. When heater switch 802 is switched on, a section of Nb wire 808, between points A and B, is driven normal, i.e. non-superconducting. Current can then be injected into field coil 46 using a field current source $I_f$ applied to points A and B. Turning heater switch 802 off traps this current in field coil 46. The current source $I_f$ may then be turned off, leaving a stable field trapped in coil 46. An end view of switch 802 is illustrated in FIG. 3H. In FIG. 3I, a side view of heater resistor 804, showing section A–B of wire 808 wrapped around the heater resistor 804 as illustrated in FIG. 3G is shown. Resistor 804 is inserted into a Teflon™ housing 810 to reduce heat loss to a surrounding liquid Helium bath 806.

EXAMPLE I

Figure 3J:
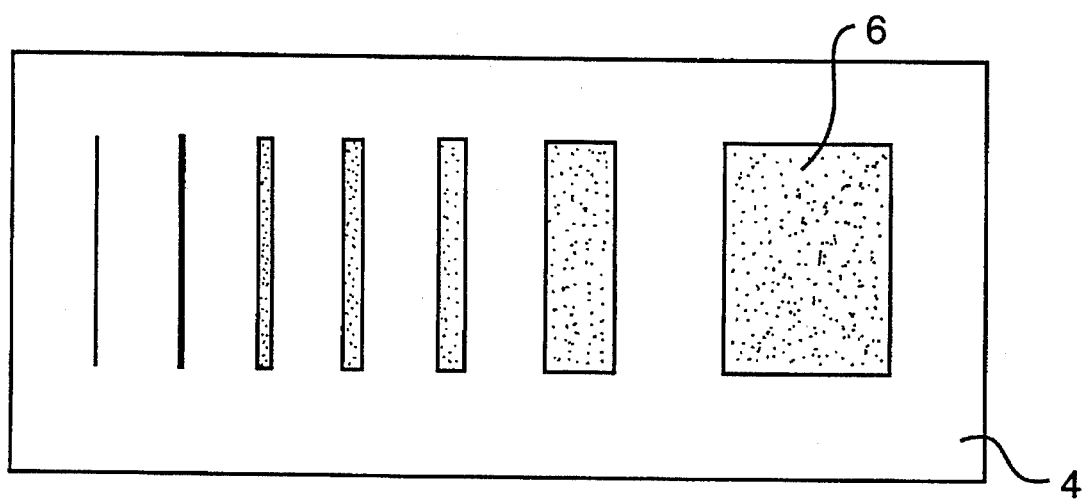
FIG. 3J is a diagram of the sample used to test the 1-D microscope of FIG. 3A.

FIG. 3J shows a schematic of a sample which was used to test the microscope. 90 nm of Pb (5 wt % In) 6 was deposited onto a Si chip 4 and was patterned with photolithography and an acid etch to form seven thin-film strips. The width of the strips are 15, 43, 92, 240, 500, 1000, and 2000 µm, respectively. For imaging, sample 42 was moved past SQUID 44, starting near the 15 µm line and finishing near the 1 mm line. The 2 mm line was unable to be imaged because it was beyond the range of the positioning mechanism.

Figure 3K:
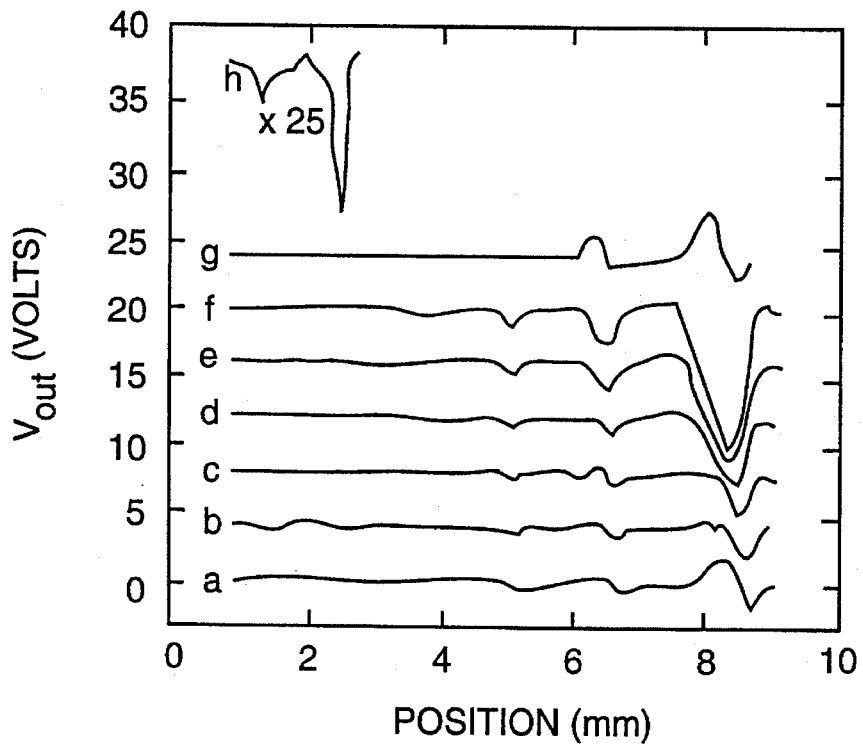
FIG. 3K is a graph of voltage versus position.

FIG. 3K illustrates a plot of the SQUID output voltage vs. sample position with successive curves offset by 4 V. Curves (a) through (h) are for applied fields of 0, 18, 36, 72, 108, 143, 0 and 750 nT, respectively.

FIG. 3K, illustrates images of the sample which were obtained by applying different strengths of magnetic field. The separation between SQUID 44 and sample 42 was measured to be 160 µm at room temperature. It is possible that the spacing may be somewhat different after cooling. For these images, a field normal to the substrate surface was applied, the flux-locked loop was closed, and then $V_{out}$ was recorded as a function of the sample position. The measurement sequence starts with curve (a) at zero applied field, proceeds with increasing field through curve (f) at 143 nT applied field, and ends at curve (g) where the field has been again reduced to zero. Curve (h) is an expanded view of the images of the 15 and 43 µm lines, taken at an applied field of 750 nT.

At smaller applied fields, the image has relatively small amplitude features, except for some prominent peaks and dips which occur over the wider lines. At higher applied fields, the images displays more prominent series of dips which are located close to the expected position of the lines, typically to better than 100 µm. For the wider lines, the width of a given dip is about the same as the width of the corresponding line.

The images may be interpreted as follows. When $I_a=0$, the first term in the $V_{out}$ equation is zero and the only position dependence comes from $\phi_x$ and the spatial dependence of $M_f$. In this case the images display only small bumps and dips because: (i) the residual field is small; (ii) except for the two widest lines, there is no trapped field in the sample; and (iii) the feedback loop is locked with n=0, as expected for a small residual field, so that the variation in n $\phi_0/M_f$ is not seen. By contrast, for large $I_a$ the large dips in the images arise from the term n $\phi_0/M_f$. This is because: (i) when the SQUID is locked at large $I_a$, $n=(I_a,M_a)/\phi_0$ is a large number, and thus n $\phi_0/M_f$ tends to dominate, and (ii) in our present arrangement $M_a I_a/M_f$ is almost a position independent constant because $M_a$ and $M_f$ get screened almost equally by the lines.

The flux trapped in the 0.5 and 1 mm lines in curve (a) was present despite cooling in a low field and was probably frozen in at the superconducting transition. Referring to FIG. 3K, it should be noted that curves (a) and (g) are different. Curves (a) and (g) were both taken at zero applied field. The primary difference was due to the fact that curve (g) was taken after the use of non-zero fields during the imaging of curves (b) through (f). During this time the features associated with the 0.5 and 1 mm lines have both increased in amplitude. This change may be attributed to the trapping of additional magnetic flux in the sample sometime during the intervening higher field scans.

From FIG. 3K the spatial resolution of the microscope may be estimated. Since the lines in the sample are separated by about 1 mm and are clearly distinguishable in the images, the spatial resolution is substantially better than 1 mm. To obtain a more precise estimate, it is noted that the image of the 43 μm line shown in curve (h) is substantially wider than 43 μm due to the limited spatial resolution of the microscope. Using the full width at half maximum of this feature, a spatial resolution of approximately 200 μm may be found. This is about the best one may achieve with the SQUID described above, and indicates that the separation between the sample and the SQUID is less than the 200 μm inner hole diameter.

With an applied field of 143 nT, and SQUID 44 positioned at the edge of the 500 μm line, the output voltage varies rapidly with sample 42 position. Dividing the noise at SQUID 44 output by the output-to-position transfer function, a position resolution of 0.5 mm Hz$^{-1/2}$ at 4 kHz was found. This equivalent motional noise is equal to the smallest sample position change which the system can detect in a unit bandwidth for this applied field, and is an upper bound on the relative motion between the sample and SQUID.

Figure 3L:
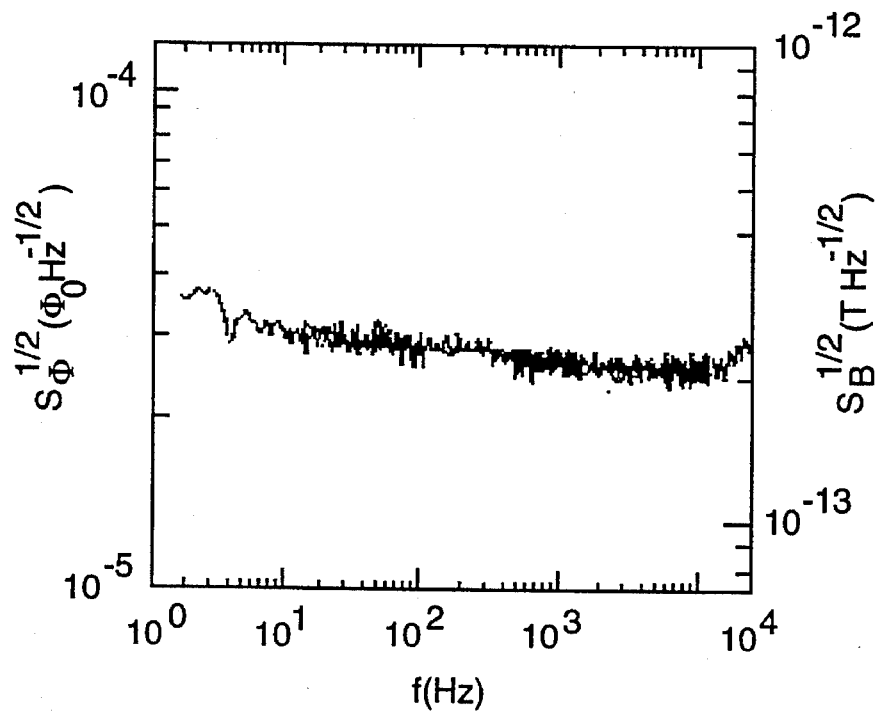
FIG. 3L is a graph of the flux noise spectral density from the 1-D microscope of FIG. 3A.

The 1-D microscope as disclosed has a spatial resolution of approximately 200 μm. A Hewlett-Packard 35665A spectrum analysis device (not shown) was used to measure the root-mean-square power spectral density of the voltage noise at the output of SQUID 44. A multiplier of $M_f/R_f$ is used to convert the output to an equivalent flux noise spectrum. The noise level of about 24μ$\phi_0$Hz$^{-1/2}$ at 4 kHz was measured and is larger than the expected value of 3μ$\phi_0$Hz$^{-1/2}$. This corresponds to a magnetic field resolution of about 1.8×10$^{-13}$ THz$^{-1/2}$. Field strengths of 0–750 nT were measured in strips of superconducting Pb. The position of a sample was monitored with a resolution of approximately 0.5 nmHz$^{-1/2}$ at a frequency of 4kHz. FIG. 3L shows a plot of the root mean square flux noise power spectral density vs. frequency when SQUID 44 is positioned between the 240 and 500 mm lines. The right hand side axis shows the equivalent magnetic field resolution of the system.

3-D MICROSCOPE

In the present invention we have disclosed a mechanism which uses sliders and wedges 60, 64, 68 (see FIG. 4A) to move the sample in two dimensions (x and y) and also allows the adjustment of the separation between the sample and sample mount 66 and SQUID 70, as shown in FIG. 4A and FIG. 4B. To minimize magnetic perturbations, the mechanism is preferably constructed almost entirely out of Delrin™ and Teflon™. The motion is controlled using three stainless steel rods, 54, 56 and 58, which are advanced using room temperature drive screws (not shown). As shown in FIG. 4C, to adjust the separation distance (d) between sample 66 and SQUID 70, on a SQUID mount 76, SQUID 70 was mounted on a spring-loaded stage 78 and a polished Delrin™ wedge 62 is used to lever SQUID stage 78 away from the sample and sample mount 66. The spring-loaded stage 78 is held against wedge deflector 62 and pivot point 74 by spring 72. The x-y mechanism gives a field of view of about 100 mm² sample while the separation mechanism has a travel of about 1 mm.

The 3-D magnetic field sensor, as shown in FIG. 2, uses a dc SQUID which is made from a single layer of YBa$_2$Cu$_3$O$_7$ (YBCO) 20. The film was laser-deposited on a SrTiO$_3$ 22.5° bicrystal substrate 22 and patterned using photolithography and a weak nitric acid etch to form a square washer with a 60×60 μm² inner hole 26 and an outer dimension of about 190 μm 24. The Josephson junctions are formed at grain boundaries in the YBCO where the two crystal orientation in the bicrystal meet 28. The measured effective magnetic field pickup area is 10$^{-8}$ m², the inductance is about 150 pH, the shunt resistance is about 2Ω per junction, and at 77K the critical current per junction is about 80 μA and the device has a maximum flux-to-voltage transfer function about 3 μV per flux quantum.

While a magnetic image is being taken, SQUID 70 is operated in a flux locked loop. Room temperature electronics 86 detect changes in voltage across SQUID 70 and apply feedback flux to the SQUID 70 to cancel any applied flux $\phi_a$. When taking an image, the voltage output of feedback electronics 86 was monitored. This voltage is related to the applied flux by the equation V=$R_f\phi_a/M_f$, where $R_f$ (typically 2KΩ) is the feedback monitoring resistance and $M_f\approx$4 pH is the mutual inductance between SQUID 70 and feedback coil 25 as shown in FIG. 2B. A subtlety of this type of imaging is that large spatial variations in the magnetic susceptibility of the sample can lead to a strong dependence of $M_f$ on the position of the sample and sample mount 66. This allows us to measure or image magnetic susceptibility as a function of position. To reduce the spatial dependence of $M_f$, it is preferable to use a small feedback coil 25 and place it as close as possible to SQUID 70. Accordingly, feedback coil 25 consists of a thin-film YBCO wire which is patterned on the SQUID chip about 500 μm from the center of SQUID 70, see FIG. 2B.

Figure 5A:
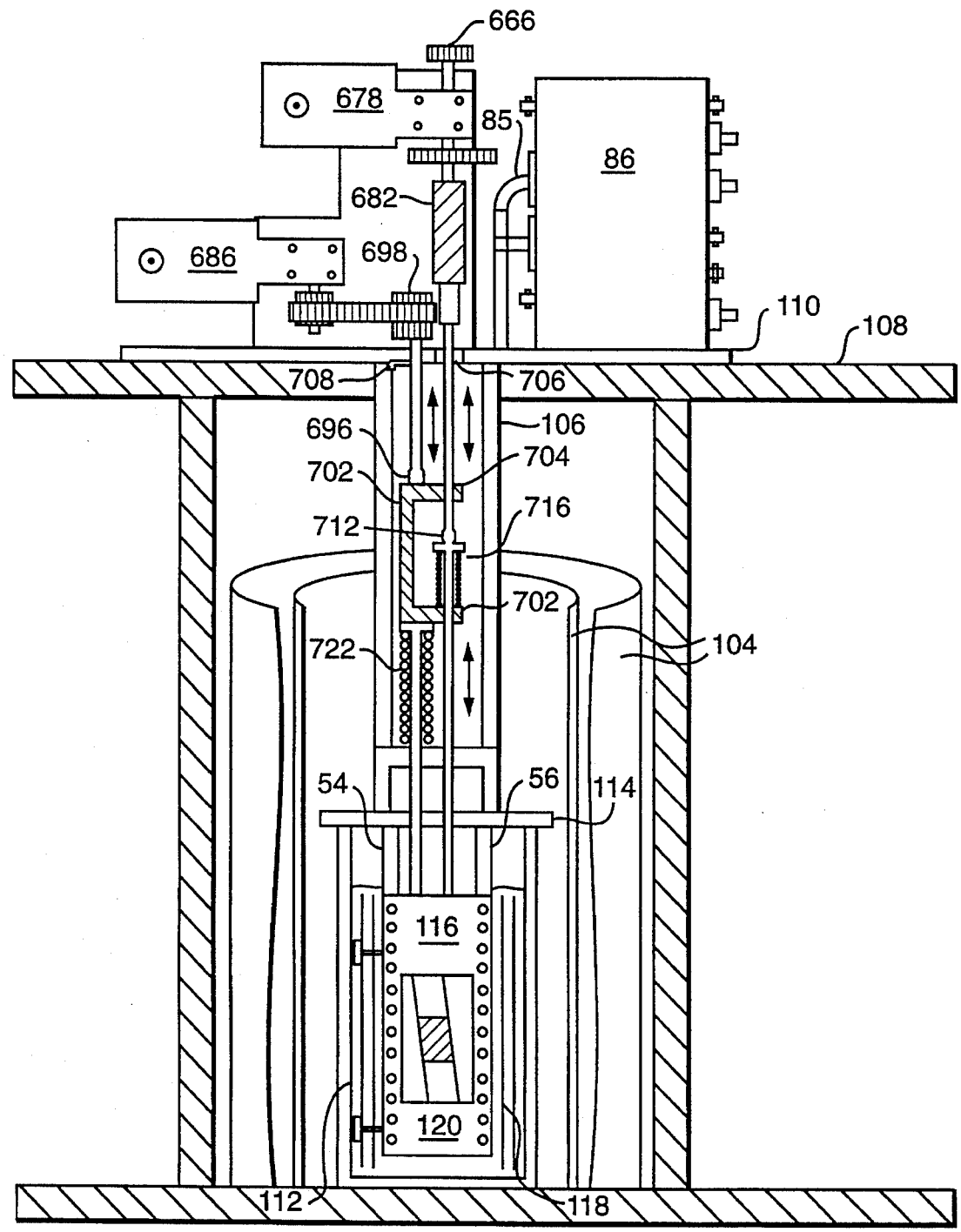
FIG. 5A is a front elevational view showing magnetic flux 3-D microscope assembly constructed in accordance with a preferred embodiment of the invention.

To take a magnetic image, sample 66 and SQUID 70 were mounted on their respective stages 78, 76 as shown in FIG. 4C and the separation distance (d) adjusted to between 10 and 200 μm. Since the size of the inner hole of SQUID 70 is about 60 μm, our spatial resolution is also 60 to 200 μm. As shown in FIG. 5A, shielding is provided from external magnetic interference, by surrounding the cryogenic sample positioning assembly with two cylindrical mu-metal shields 118 which are bolted directly to assembly 644 of FIG. 5B and 5C. The assembly and shields are then inserted into a liquid nitrogen dewar 112 which is surrounded by two room-temperature mu-metal shields 104. To take an image, SQUID output Voltage V and position x, are recorded, as the sample is scanned in the x direction for various values of y.

Looking at FIG. 6, the SQUID output V and the position (x,y) are sampled with an analog to digital converter 260 located in a multifunction data acquisition device (MDAD), and stored in a computer 200 where the data may be converted to a line plot, gray scale image or false color image using commercial software. Computer 200 is coupled to the MDAD converter 260 via a bi-directional buss 264 which is coupled to electronics package 86 on the magnetic microscope 108 via a second bi-directional buss 262. Electronics package 86 is electrically-interconnected to wire feedback coil 25, field coil (similar to that of field coil 46 in FIG. 3A for the 1-D microscope) and SQUID 70 through conduit 85. Electronics package 86 receives data from computer 200 to control stepper motors (not shown), so as to move the sample and sample mount 66 and/or SQUID 70. The stepper motors may be vibration isolated and assembled in a similar fashion as in that of the 1-D microscope as illustrated in FIG. 3B. Two separate stepper motors, for the x and y axes, are incorporated instead of only one stepper motor 416 as is disclosed for the 1-D embodiment. The Z motion is controlled manually by turning knob 606 (see FIGS. 5B and 5C).

Turning to FIG. 6, computer 200 is coupled to a storage device 240 via a bi-directional buss 266. The storage device 240 may comprise various types of storage such a magnetic, optic or magneto-optic devices. Peripheral devices 210 are connected via a third buss 268 to communicate resulting data. The peripheral devices can be printers, plotters, or other data processing systems. A keyboard 220, a display screen 280, and mouse 230 are also included to aid in user interfacing and displaying images. This system is capable of acquiring data from the microscope, controlling the positioning of the x,y and z stepper motors, determining positions from data acquired from the potentiometer transducing devices, adjusting the positions based on the information gathered, providing test data to the microscope and adapting the testing criteria for the microscope. Further, computer 200 may provide output, both visual and printed of the related data.

Figure 5B:
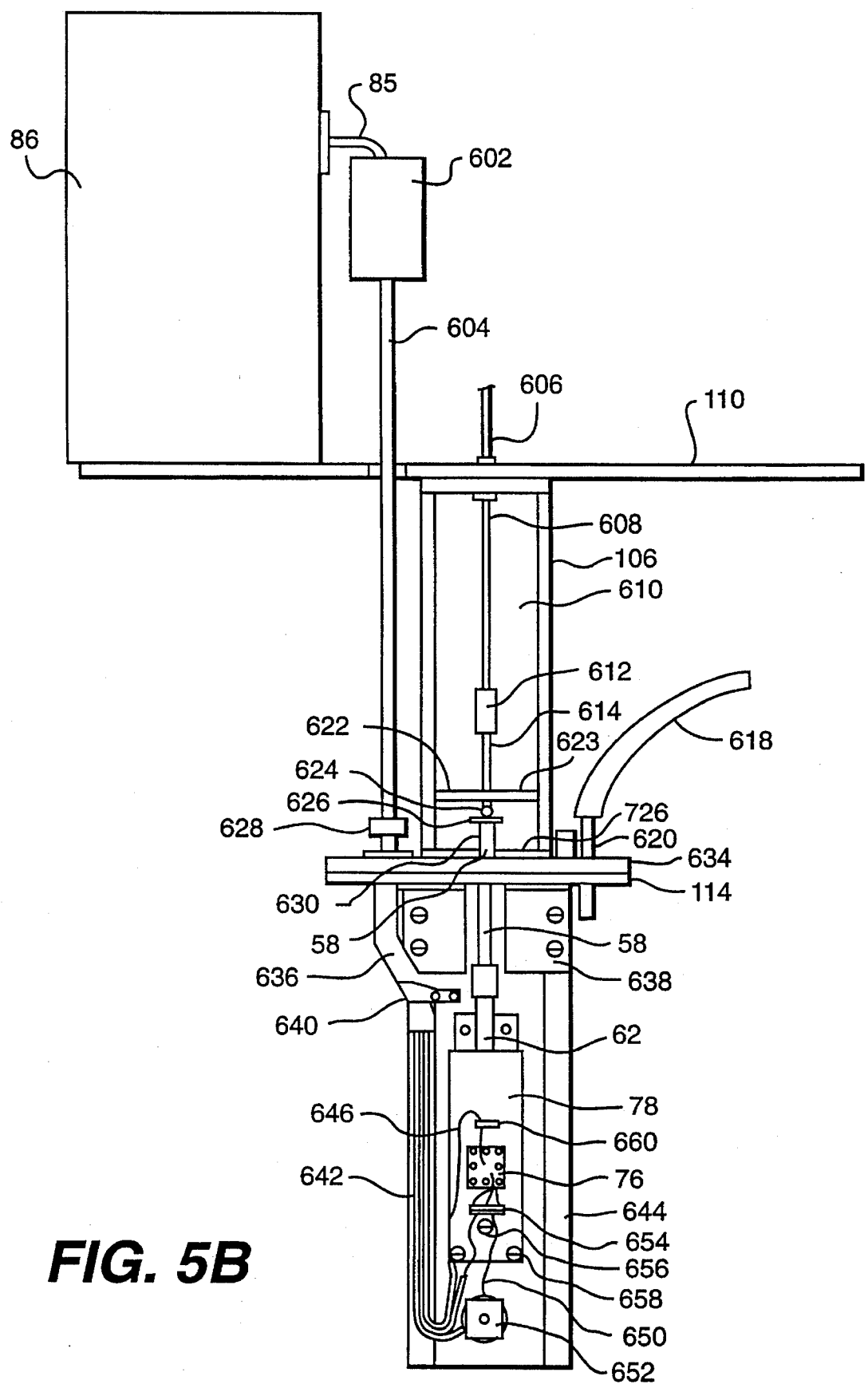
FIG. 5B is a diagram of the 3D high Tc microscope assembly of FIG. 5A, for clarity, the x and y drive assemblies and position monitors are not shown, i.e., only the Z drive is shown.

Turning now to FIG. 5B, this is a detailed schematic front view of the 3-D high $T_c$ microscope assembly. For clarity, the magnetic shields and the x and y assemblies and position monitors have not been drawn in this view; only the z-drive has been included. Top plate 110 is used to support motion controls and room temperature electronics boxes 86, 602. Boxes 86 and 602 are connected via a conduit 85. Z-drive shaft 606 is coupled by a coupling device 612 to a number 6–72 drive screw 614. Drive screw 614 passes through a threaded hole 622 in a support plate 623. As z-drive screw 614 advances, a brass pushing nub 624 applies pressure against brass pushing plate 626. Pushing plate 626 is held against nub 624 by a return bias spring 630 pushing against plexiglass cover plate 634 for Dewar 112. The bottom central surface of pushing plate 626 is fitted to z-pushing rod 58, made of stainless steel. Plexiglass plate 634 is mounted to styrofoam plate 114 for sealing the top of liquid nitrogen dewar 112. A tube 620 passes through plates 114 and 634 to allow passage of liquid nitrogen, into Dewar 112. Fill hose 618 is shown connected to tube 620. Pushing rod 58, passes through plates 114 and 634 and end plate 726, for the aluminum chassis, into Dewar 112. The top end of wedge 62 is attached to the lower end of pushing rod 58.

The adjustable SQUID mounting platform 78, preferably made of Delrin™, is held against the x-y-z cryogenic positioning assembly support 644 by means of pivot screws 658 and bias spring 656. Positioning assembly 644 is mounted to plate 114 by a stainless steel mounting bracket 638. A number of components are mounted to SQUID mounting platform 78. These components include wiring plug and socket 660; SQUID mount 76; wiring plug and socket 654; wiring for the output of SQUID 650; and a bolt for return bias spring 656 for the z-platform. Positioning assembly 644 provides a supporting surface for the SQUID output impedance matching transformer 652. The SQUID wiring 642 and sample wiring are housed in a thin-walled stainless steel guideway 636. Guideway 636 is attached to positioning assembly 644 by a restraining clip 640. Steel guide 636 passes through plates 114 and 634, where guide 636 connects to a quick-connect fitting 628 for SQUID wiring tube 604. SQUID wiring tube 604 is preferably made of Cu and is connected to a wiring box 602 for the SQUID and sample wiring.

Figure 5C:
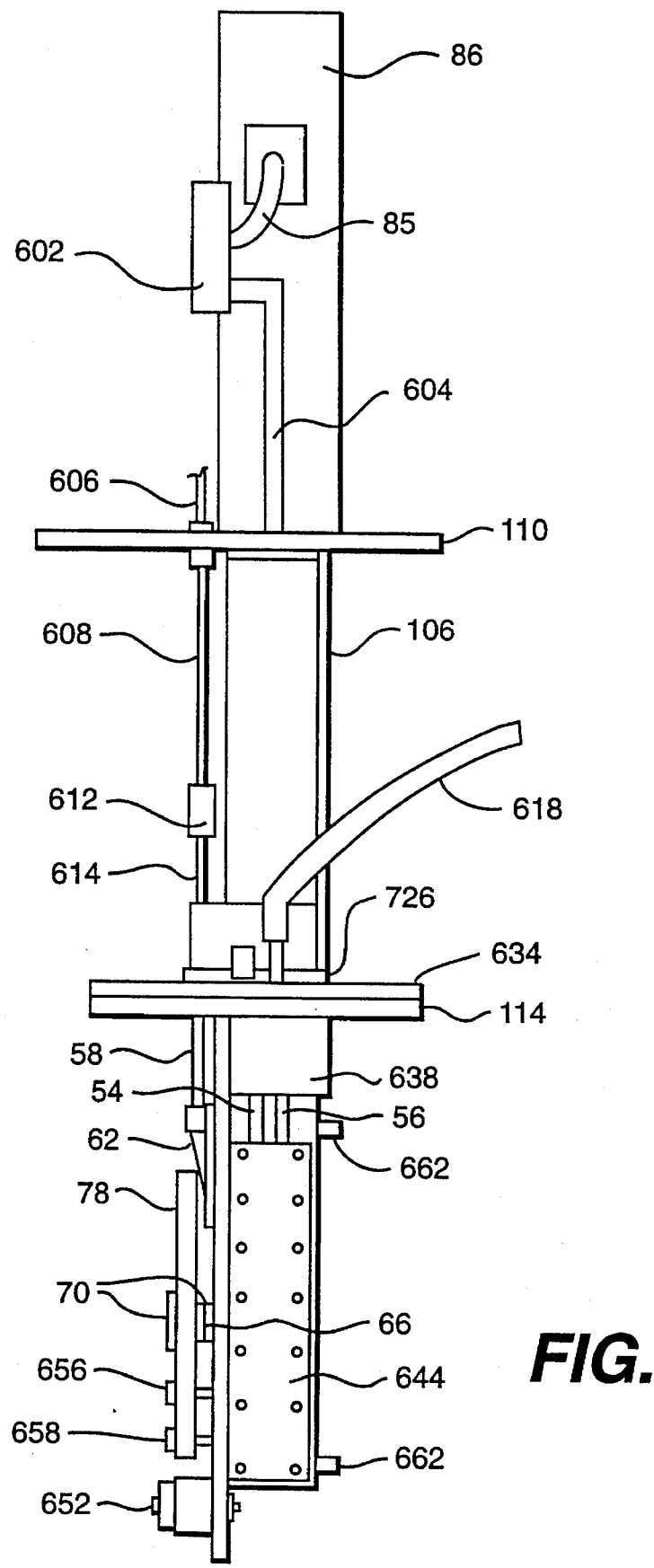
FIG. 5C is a side elevational view of the 3D high Tc microscope, having only the Z drive is shown.

Now turning to FIG. 5C, a side view of the 3-D microscope assembly is shown. For clarity, the x and y drive assemblies have been excluded. Push rod 58 is advanced or retreated by the rotation of drive screw 614. This in turn moves wedge 62 up or down with push rod 58. The motion of wedge 62 causes SQUID mounting platform 78 to move away or towards the sample and sample mount 66, thereby altering the separation between SQUID 70 and sample 66. SQUID mounting platform 78 pivots about screws 658 and is held against wedge 62 by spring loaded screw 656. The elements 658 and 656 are one embodiment of parts 72 and 74 in FIG. 4C.

The x-pushrod 54 and y-pushrod 56 are shown for relative positioning. They are within the X-Y cryogenic positioning assembly 644. At either end of assembly 644 there are two mounting brackets 662 for high permeability magnetic shielding cylinders 118.

Figure 5D:
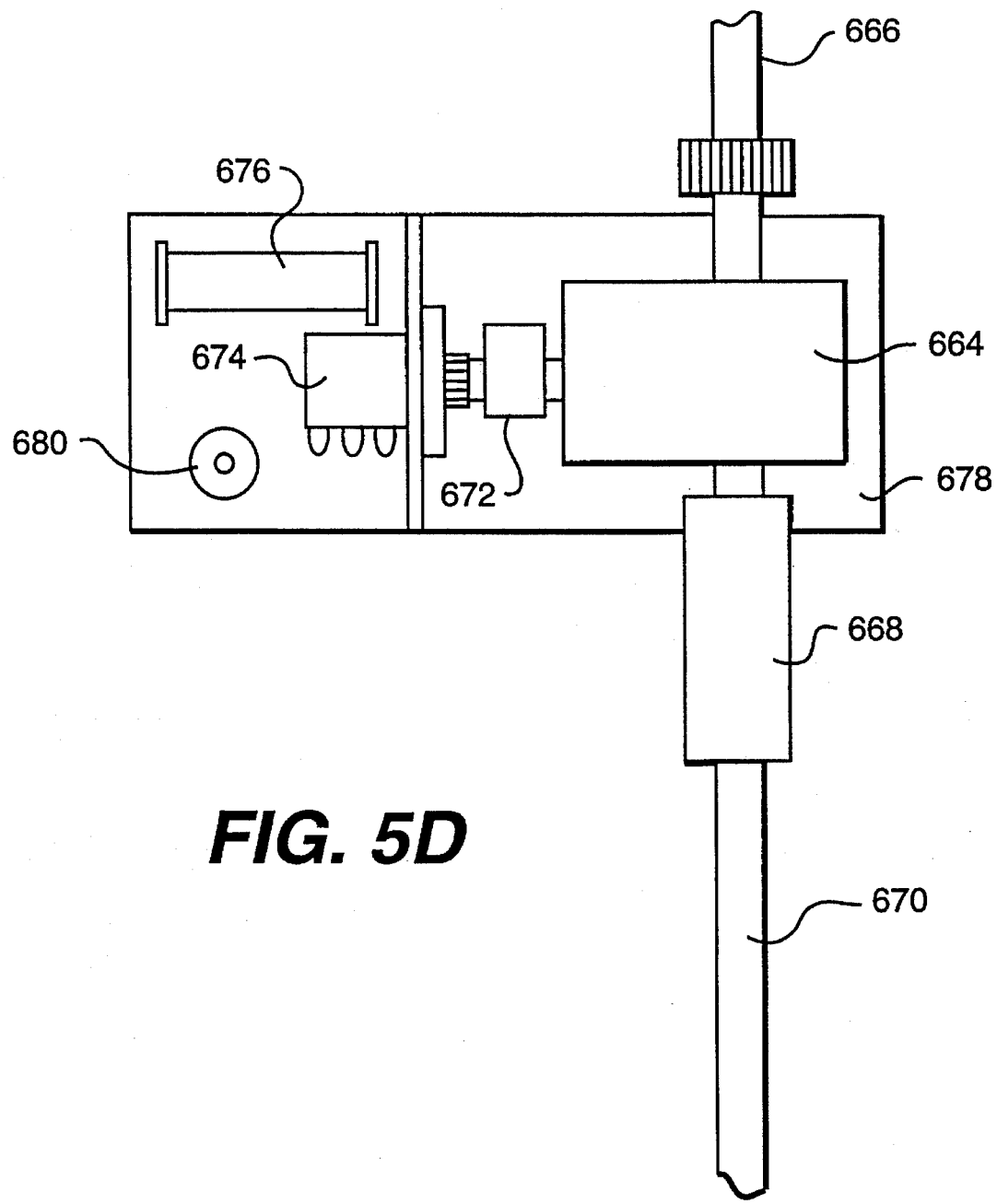
FIG. 5D is a schematic of the placement of the main components in the Y drive position transducer.

FIG. 5D is a schematic layout of the placement of the main components in the y-drive position transducer. The x and z systems incorporated similar systems. The y-drive shaft 666 is connected to, a stepper motor assembly not shown and is coupled to a 12 to 1 gear reduction assembly 664. A 10 turn potentiometer 674, with a battery 676, is coupled through a shaft coupler 672 for 10 times reduction output from reduction gear assembly 664 to drive shaft 666. Reduction gear assembly 664 is coupled through a shaft coupler to the final y-rotary drive shaft 670. A mount 678 is provided to support the battery 676, potentiometer 674, a BNC connector 680, coupling means 672 and the gear box 664.

Figure 5E:
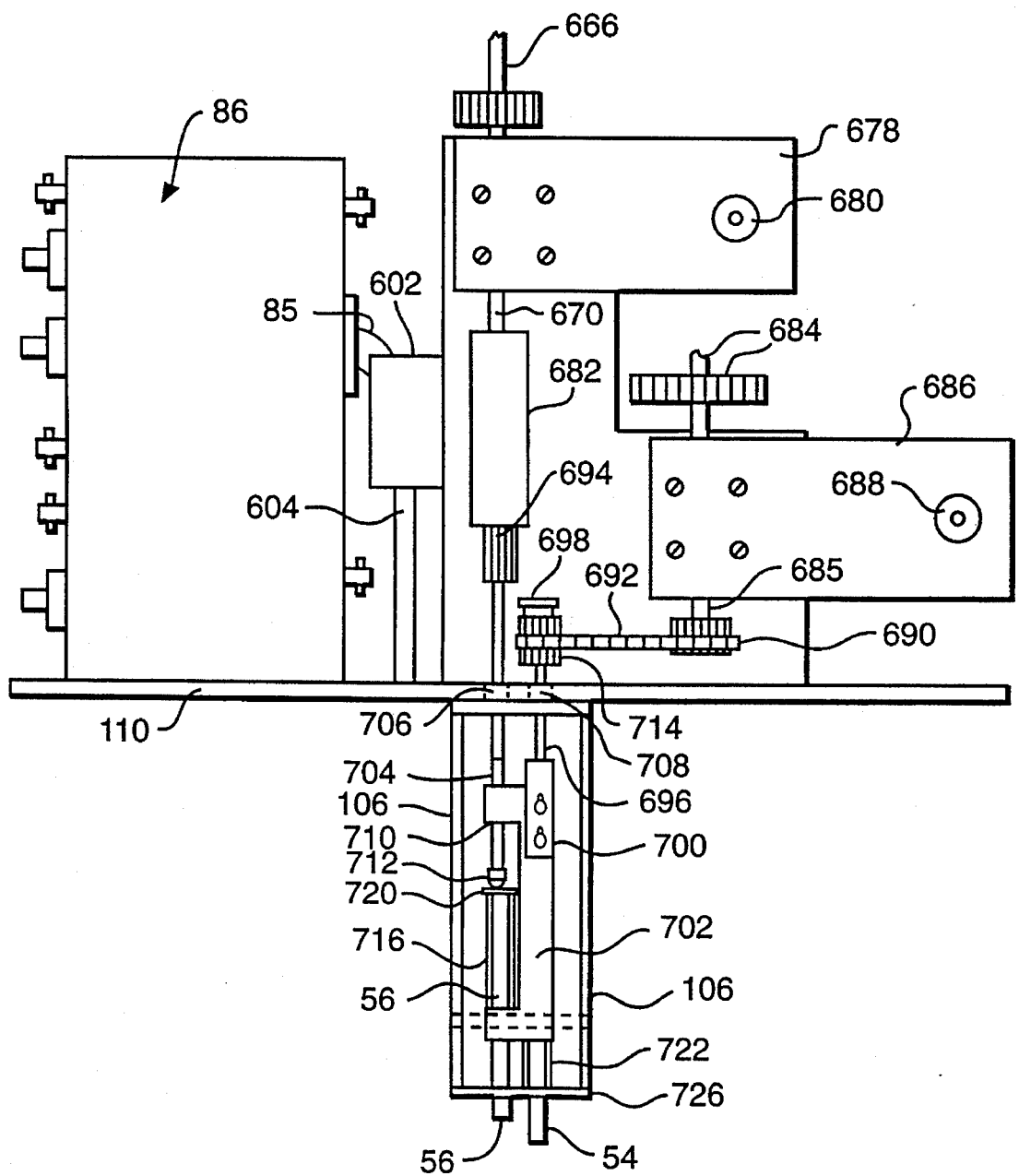
FIG. 5E is a front elevational view of the position transducers, coupling assemblies and feedback electronics box.

Turning to FIG. 5E, a detailed view of the room temperature portions of the x and y drive assemblies and position monitors is illustrated. The y-drive functions as follows. The y-drive shaft 666 rotates shaft 670 and splines 682, 694 and advances drive screw 704. Drive screw 704 passes through hole 706 in the top plate 110. Splines 682 and 694 take up the change in length of the shaft when drive screw 704 as well as when x-drive screw 696 advances. The end of the y-drive screw, number 5–40 type, is terminated with a brass nub 712 which pushes against push plate 720, which in turn advances y-push rod 56. Push plate 720 is held against nub 712 by a stainless steel return spring 716 fitted around push rod 56. The top of spring 716 is in contact with the under surface of plate 720 and the bottom end of spring 716 is supported by a c-bracket 702. The y-position transducer assembly, as shown in FIG. 5D, monitors the rotation of y-drive shafts 666 and 670. This rotation produces a voltage at the BNC output 680 which is linear in the sample y-position. The x monitoring system is enclosed in assembly 686. The x-position data signals are taken out of BNC connector 688. The z monitoring system function in similar manner and is not shown, nor will it be discussed in detail.

The x drive system works in the following manner. The x-drive shaft 684 rotates shaft 685 and advances drive screw 696, through a toothed belt 692 and pulley 690 and pulley 714. Drive screw 696 passes through threads 708 in top plate 110. The end of the x-drive screw, number 5–40 type, is terminated with a brass nub not shown which pushes against a c-bracket 702 which in turn advances x-push rod 54 as well as rod 56. A retaining clip 700 is used to hold x-drive pushing nub 712 against c-bracket 702. The bottom of the c-bracket is biased by a stainless steel return spring 722 fitted around push rod 54. The top of spring 722 is in contact with the under surface of c-bracket 702 and the bottom end of the spring 716 is supported by end plate 726 of aluminum support chassis 106. Aluminum support chassis 106 is bolted to the top of the plexiglass dewar cover 634 and 114. Pushrods 54 and 56 pass through holes in the end plate 726.

Figure 5F:
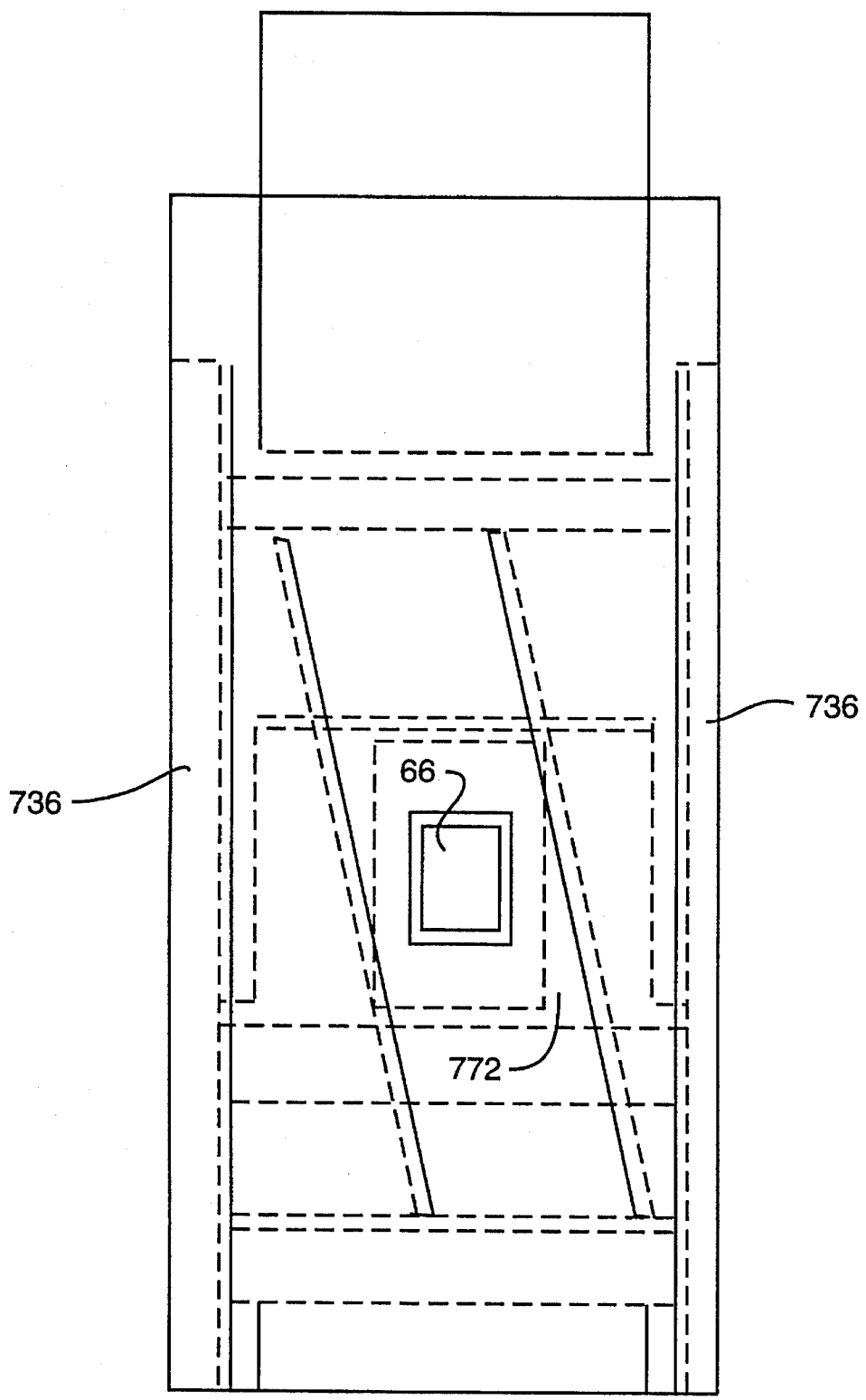
FIG. 5F is a front elevational view of the cryogenic positioning assembly, having the x/y-slider being shaded.

Referring to FIG. 5F, a detailed front view of the cryogenic positioning assembly, as shown in FIG. 4A, 4B and 4C is illustrated. The shaped area 772 represents the Teflon™ x and y sliders. This fits between the x-slider and the y-slider and carries the sample and sample mount 66. The Delrin™ support box 736 holds the slider mechanism together.

Figure 5G:
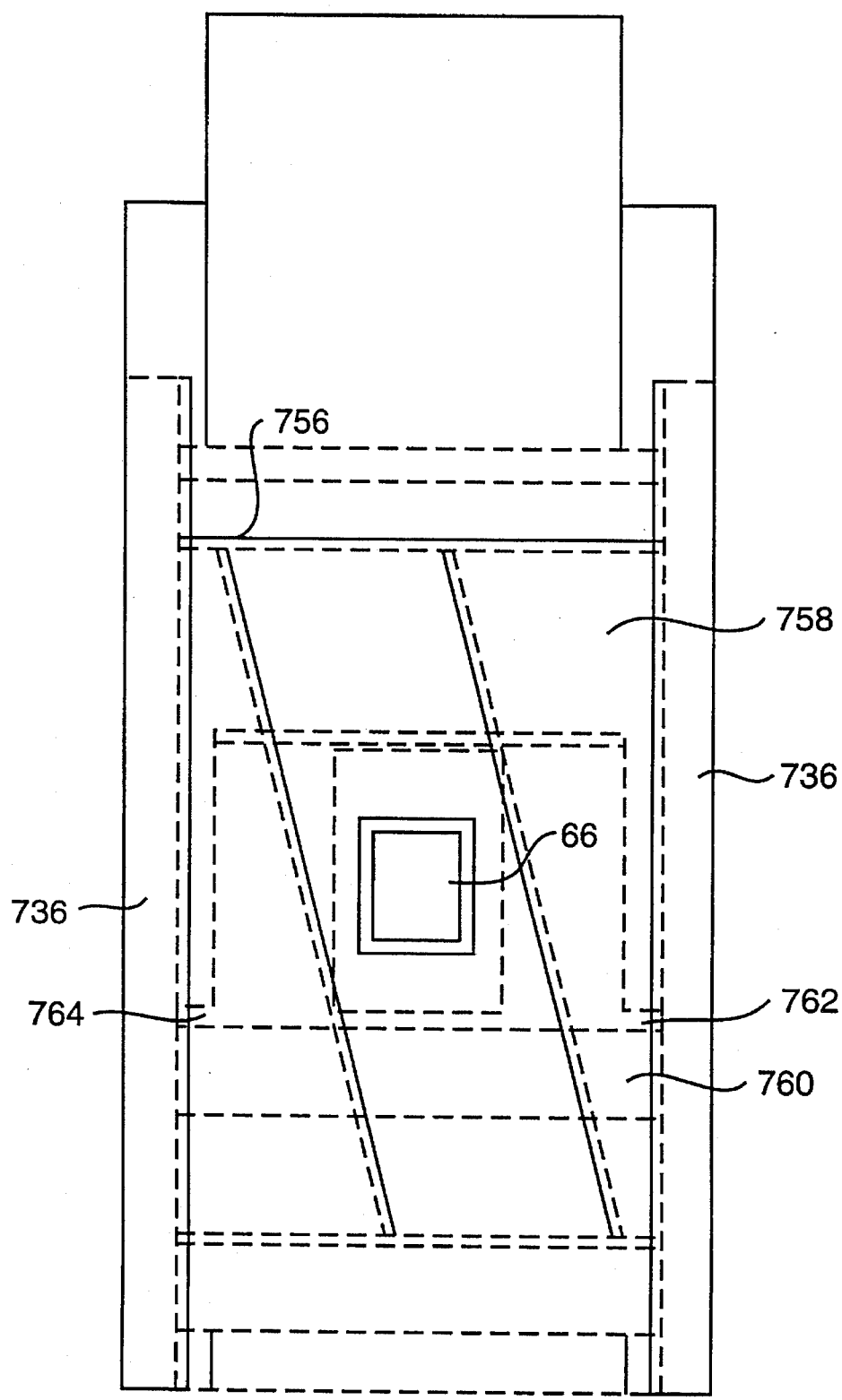
FIG. 5G is a front elevational view of the cryogenic positioning assembly, having the x-slider being shaded.

Turning now to FIG. 5G, a detailed front view of the cryogenic positioning assembly is illustrated. The Delrin™ x-slider is shown as parts 758 (top) and 760 (bottom). The two halves constitute part 64 in FIGS. 4A and 4B. The sample and sample holder 66 is slidably mounted inside the x-slider 64. The top part of the x-slider 758 is attached to the bottom x-slider 760 by means of spring loaded screws 764 and 762. The combined unit 64 is slidably movable within a set of channels 736. Push rod 54 is attached at point 756.

Figure 5H:
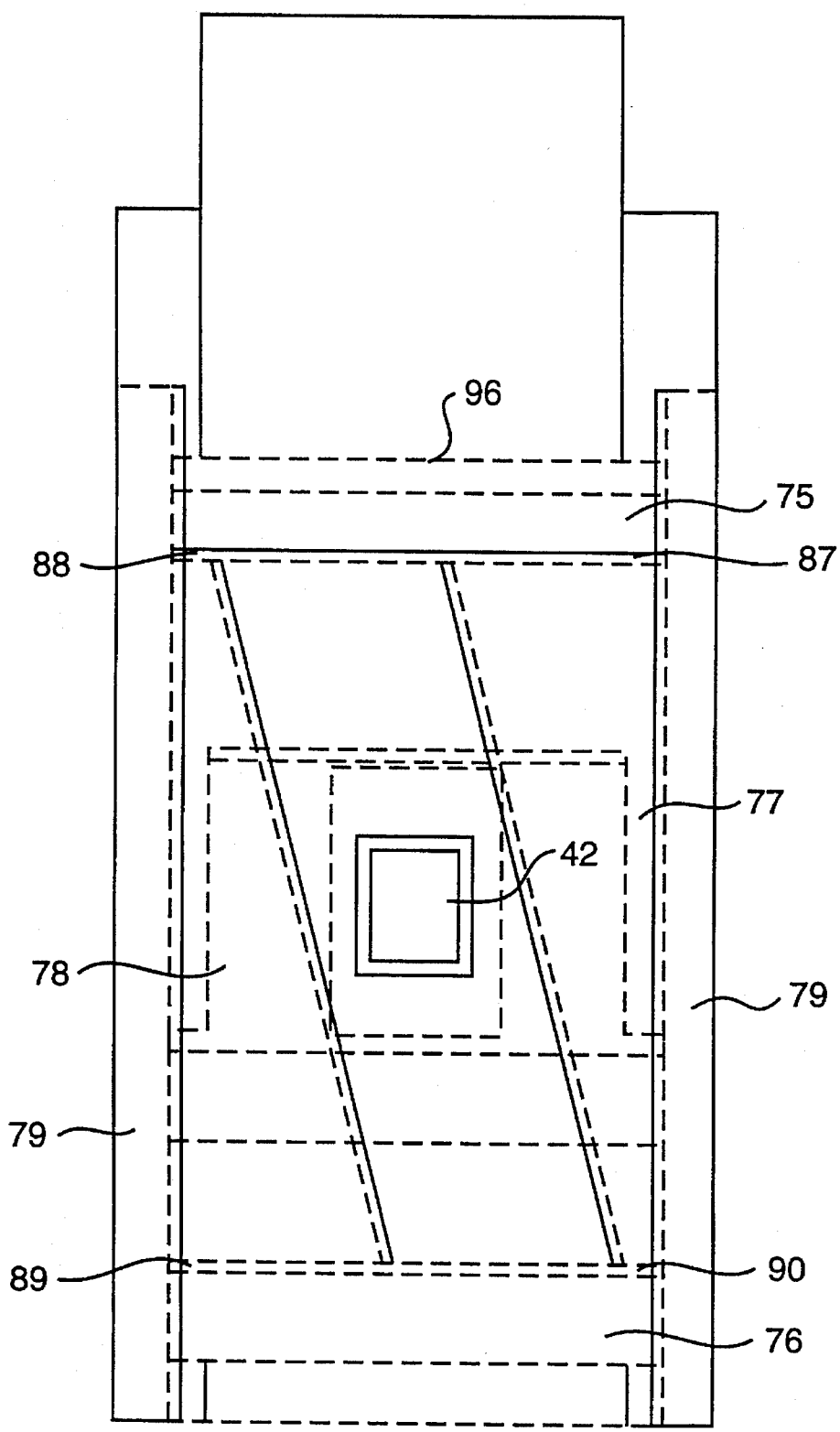
FIG. 5H is a front elevational view of the cryogenic positioning assembly, having the y-slider being shaded.
Figure 5I:
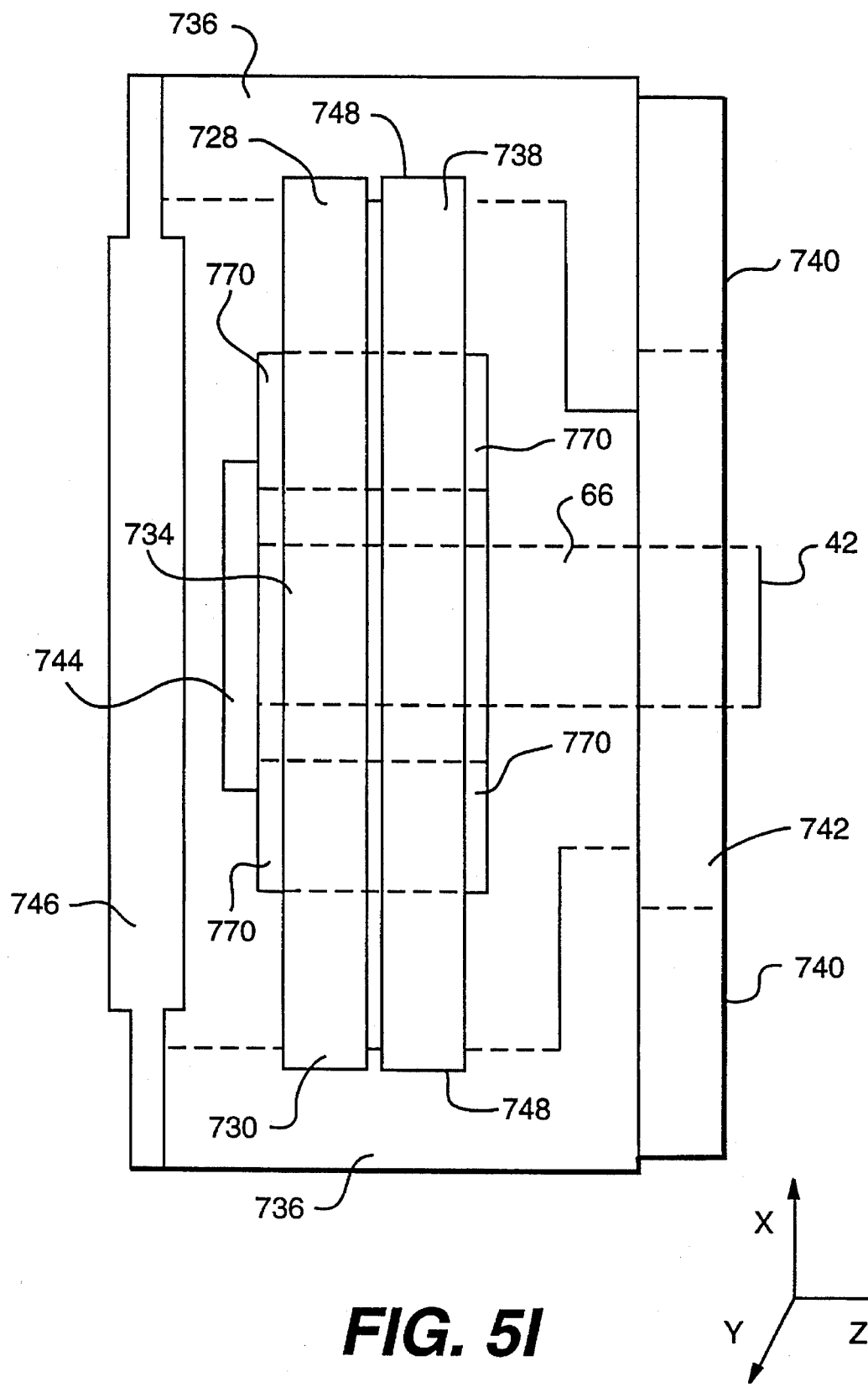
FIG. 5I is a top view of the cryogenic positioning assembly.

Referring to FIG. 5H and FIGS. 4A and 4B, a detailed front view of the cryogenic positioning assembly, with the y-slider shaded, is illustrated. The y-slider 60, as shown in FIGS. 4A and 4B comprises a top 75, a bottom 76 and two side members 77 and 78. They are joined by spring loading screws 88, 90, and screws 87 and 89. This combined unit 60 slides in two Teflon™ channels mounted in Delrin™ support assembly 736, see FIG. 5I. Push rod 56 is attached at point 96. The sample and sample holder 66 slidably moves within composite unit 60.

With this arrangement, it is possible to image a variety of samples. The following are a number of examples:

EXAMPLE I

Figure 7A:
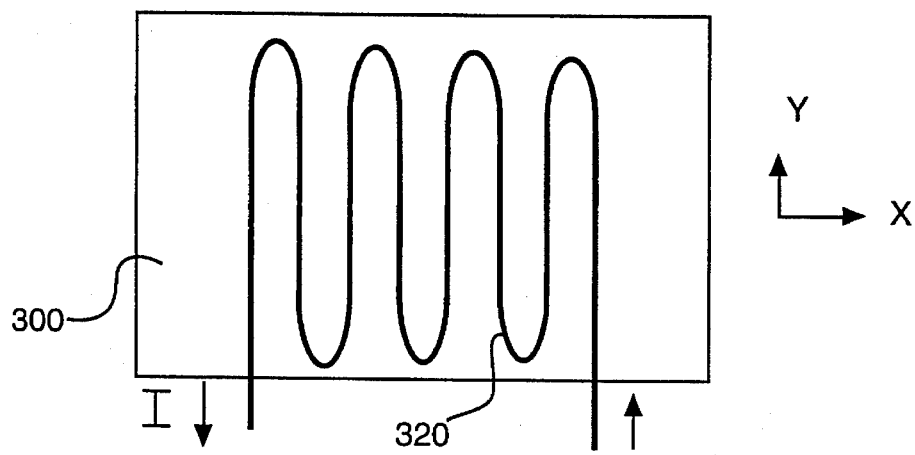
FIG. 7A illustrates the layout of a wire sample.
Figure 7C:
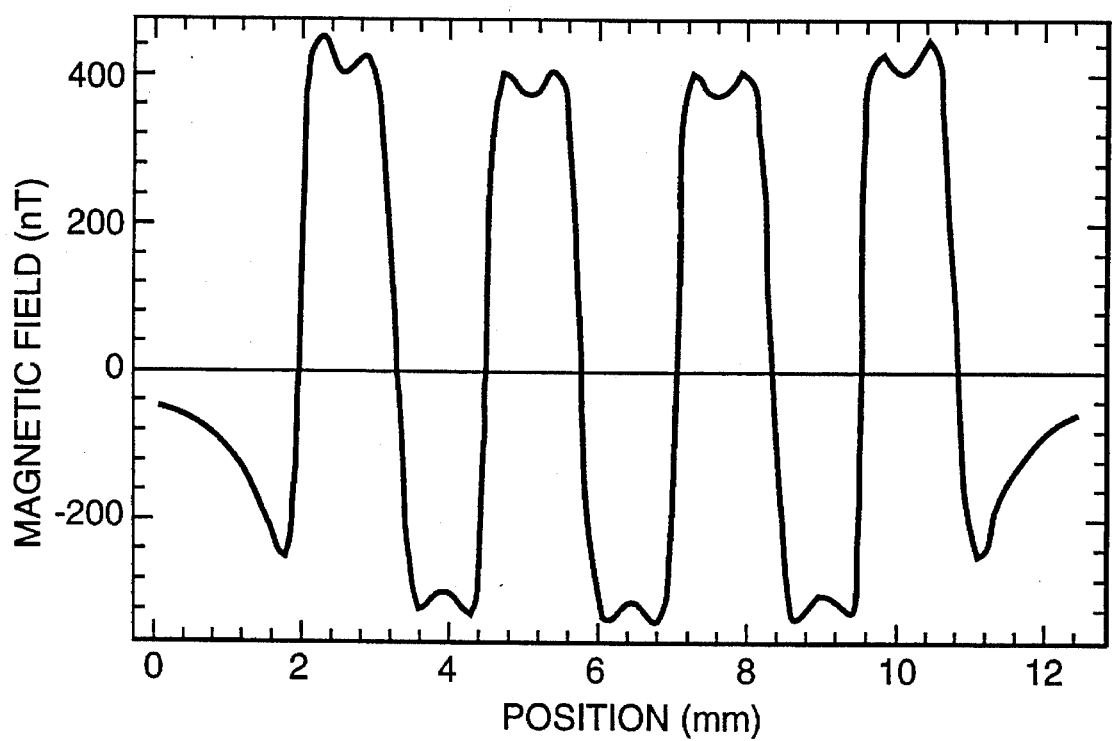
FIG. 7C is a plot of 1-D expected data.
Figure 7D:
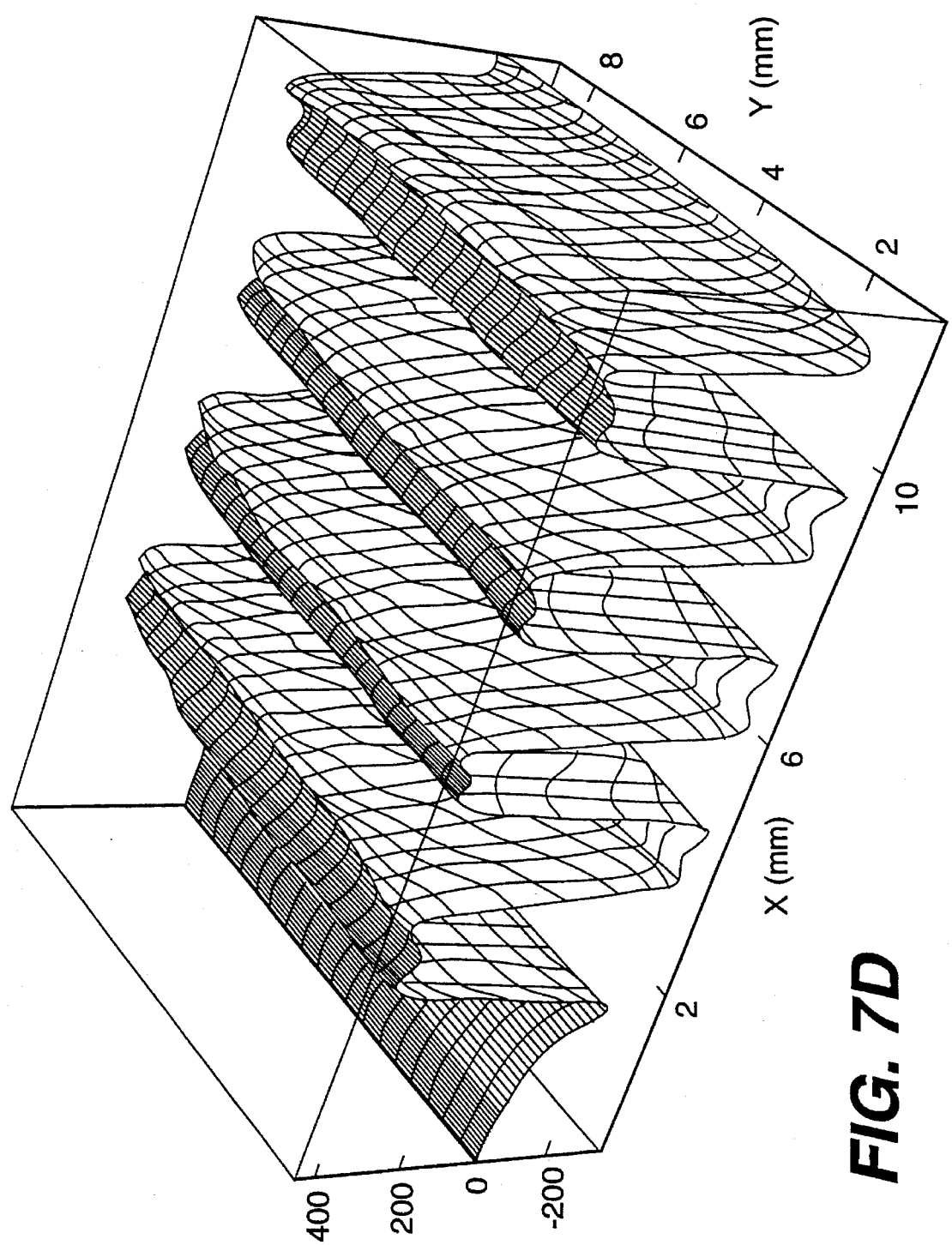
FIG. 7D is a plot of position versus magnetic field for the 3-D data of the wire sample with applied current of 800 mA.

As shown in FIG. 7A, a 150 μm diameter copper wire bent into a meander pattern and glued to the surface of a plastic holder (300) is illustrated. FIG. 7B illustrates the resulting magnetic image taken at a Squid to sample separation of d=200 μm with a current of 0.8 mA flowing in the wire. The image covers an area of about 6×12 mm$^2$ and is produced from 20 individual scans in the x direction, which are shown as the mesh-lines running from left to right at different values of y in FIG. 7D. In this image, the SQUID is sensitive only to the z component of the magnetic field, $B_z$, which varies from about −0.3 μT to 0.3 μT. The observed pattern is in good agreement with the expected field configuration and no noise is evident in the image. FIG. 7C shows a plot of the expected results from the magnetic microscope in a 1-D scan.

EXAMPLE II

Figure 8A:
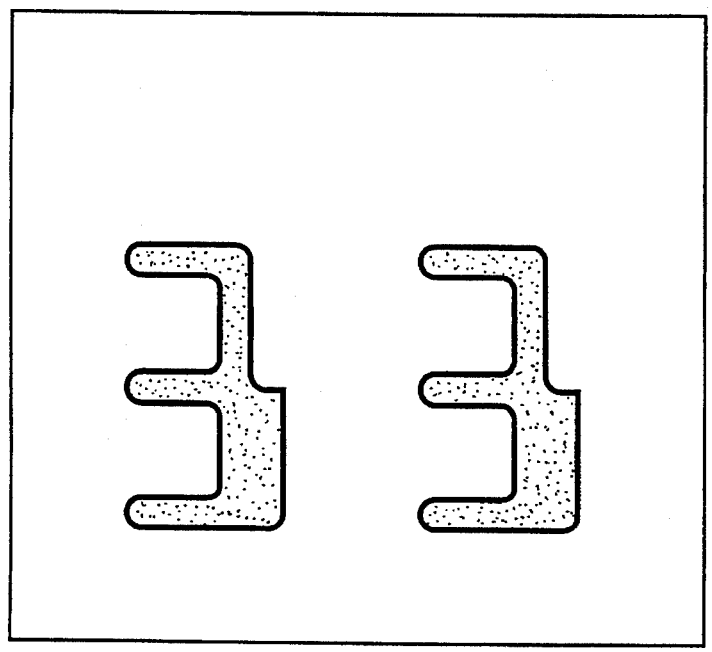
FIG. 8A illustrates the number 33 printed in ferromagnetic ink on a deposit slip.
Figure 8B:
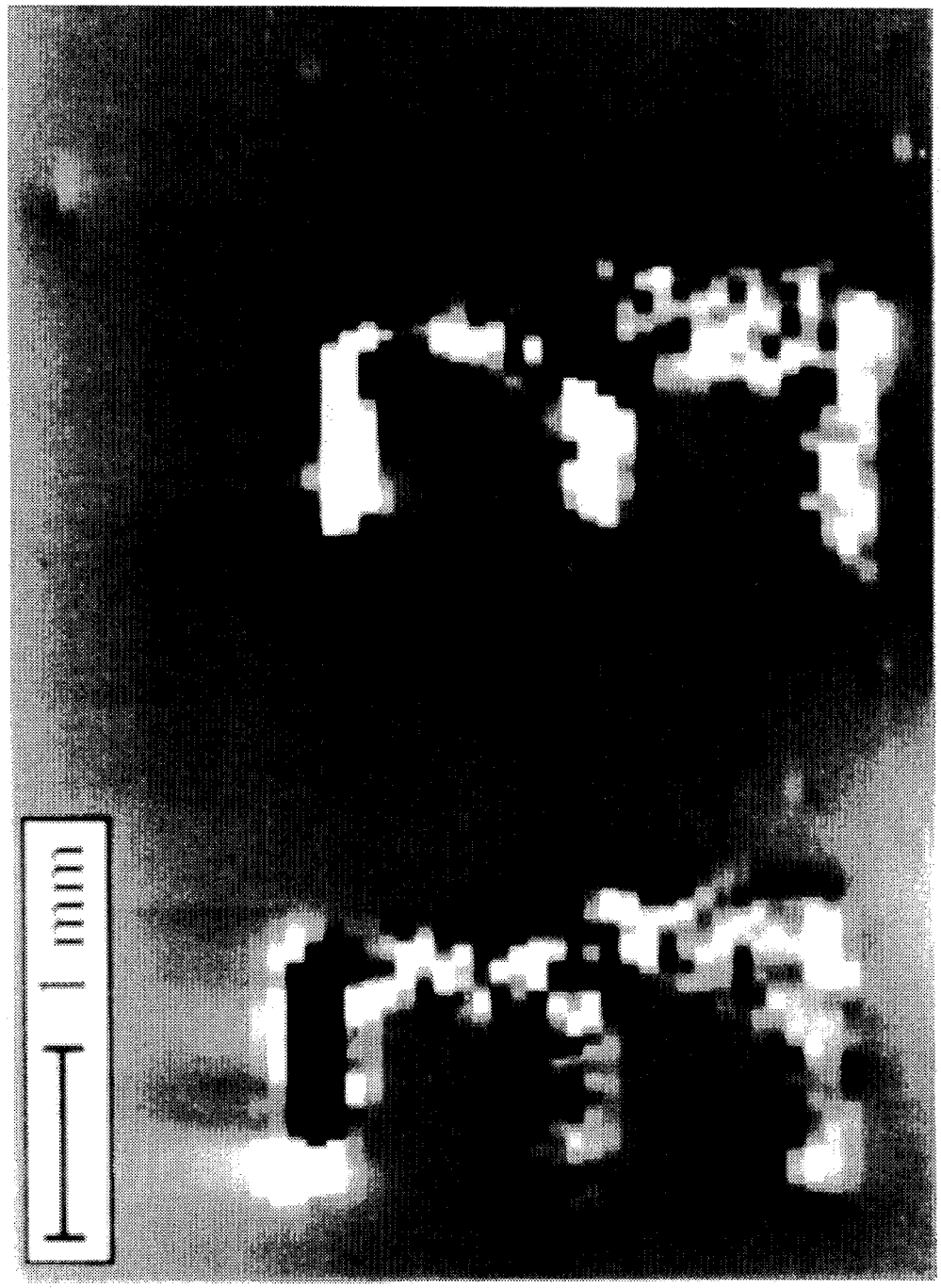
FIG. 8B illustrates the magnetic image of the ferromagnetic ink sample of FIG. 8A.

Another common and easily imaged type of sample consists of ferromagnetic ink patterns on paper, as illustrated in FIG. 8A. To facilitate automatic processing, commercial banks often use ferromagnetic ink to print account information on checks. FIG. 8B shows a magnetic image of the number 33 from a small region of such a check. The image is taken in zero applied field with d=160 μm and shows the remnant magnetization in the sample. The image was constructed from 51 scans which are spaced approximately 100 μm apart in the y direction. The magnetic field normal to the sample, $B_z$, is shown as a gray scale running between −370 nT (black) and 370 nT (white). The tops of the numbers appear to be large single domains of magnetization, while the remaining portions exhibit less ordered structure. The dipolar nature of the domains is evident throughout the image as a clustering of light and dark patches corresponding to field lines emerging from one end of a domain and returning to the other end.

EXAMPLE III

Figure 9A:
FIG. 9A illustrates a picture of George Washington's face on a $1 bill.

FIG. 9A shows a photograph of another ink sample, the portrait of George Washington from the front of a U.S. one dollar bill. The bill is printed using ferromagnetic ink. FIG. 9A is a close-up picture of the part of the bill used as a sample: George Washington's portrait consists of many short segments of ink. These short segments tend to form tiny permanent magnets, or magnetic dipoles, which have their north and south poles pointing along the surface of the bill.

Figure 9B:
FIG. 9B illustrates the magnetic image of a the face of George Washington as illustrates in FIG. 9A.

The gray-scale magnetic image of George Washington's portrait is shown in FIG. 9B. Note that most of the image is composed of black and white spots. Each black and white pair of spots in the image is actually due to an individual magnetic dipole formed by one of the ink line segments. The light patch is where the magnetic field lines emerge from the surface at the dipole's north pole and the accompanying dark patch is where the field lines wrap back into the surface at it's south pole. This dipole signature is seen readily throughout the image; note especially the eye, lips and spots in the cheek.

EXAMPLE IV

Figure 10A:
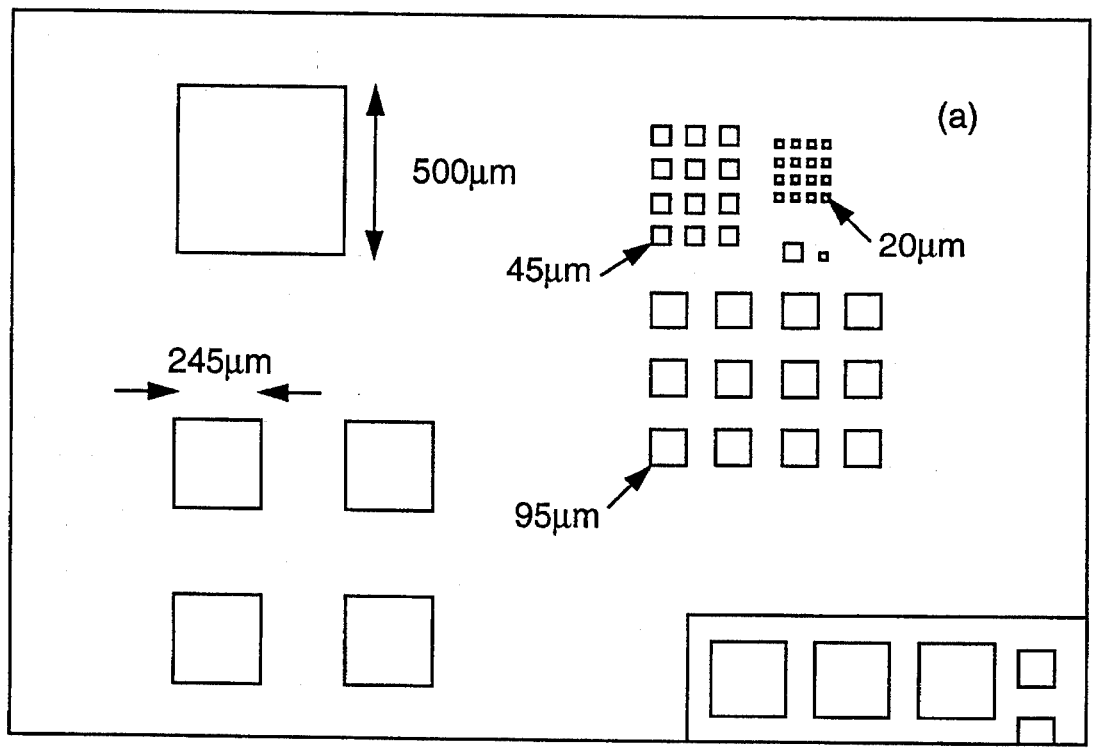
FIG. 10A is a schematic of patterned thin-film of $YBa_2Cu_3O_7$ superconductor.
Figure 10B:
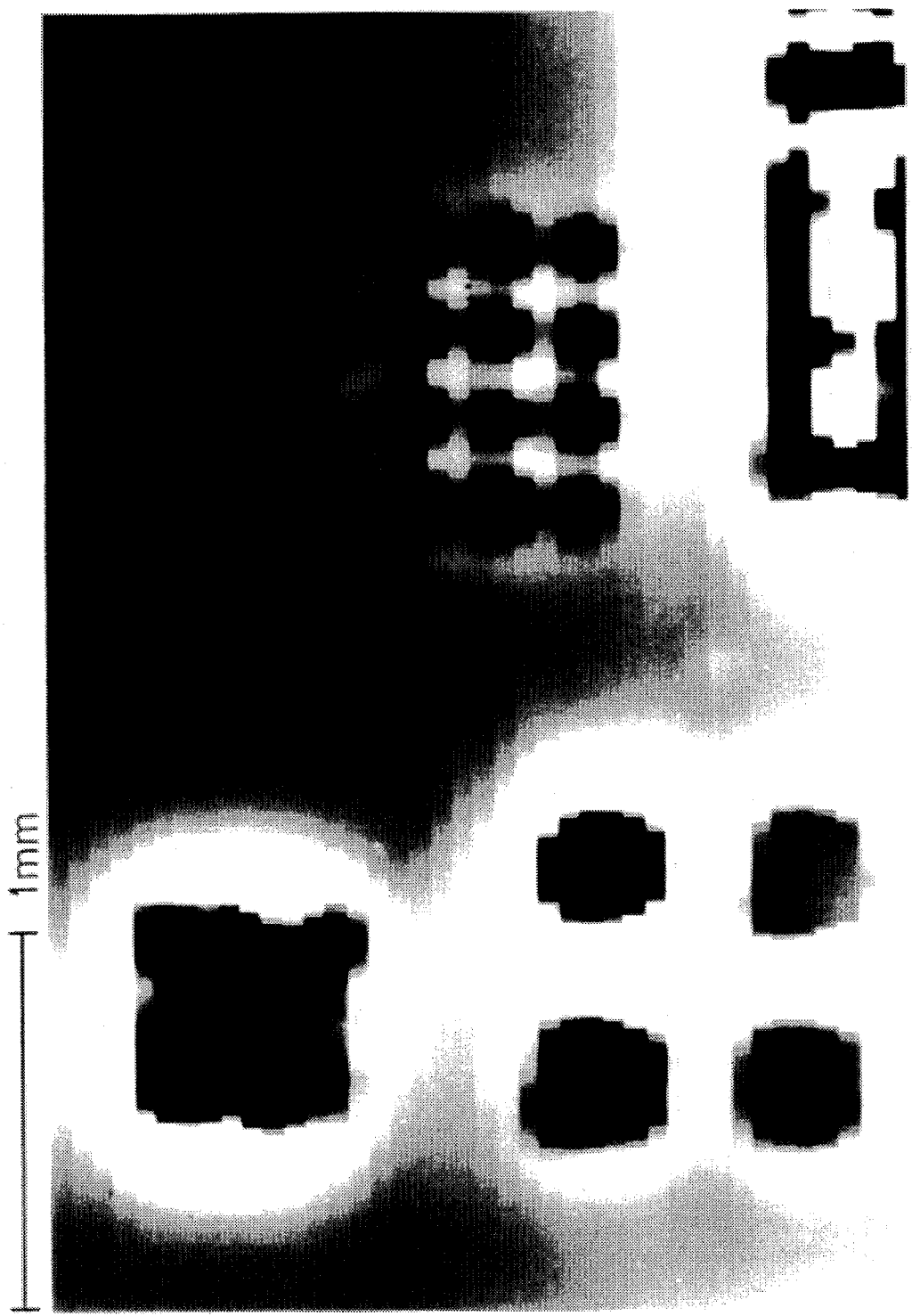
FIG. 10B illustrates the magnetic image of the sample of patterned $YBa_2Cu_3O_7$ superconductor in an applied field of about 6 μT.

Another sample consists of a thin-film of superconducting YBCO shown in FIG. 10A. This shows the configuration of the sample, which has been patterned into a series of boxes of different widths, and FIG. 10B illustrates the resulting magnetic image of the sample at 77K in an applied field of about 6 μT. For this image, d=70 μm and we find a spatial resolution of about 80 μm corresponding to the full width at half maximum of the sharpest feature in the image. The horizontal scan lines which make up the image are spaced 50 μm apart in the vertical direction. The dark patches are regions where the field is shielded by the superconductor, and hence smaller than the background applied field, while the lighter areas around the superconducting material are the fringing fields enhanced by the edges of the YBCO.

From this image, it may be seen that the largest box, 500 μm on a side, is not perfectly superconducting. Rifts are clearly apparent in the lower edge where the field protrudes. It should also be noted that it is possible to see the faint impression caused by the screening of the applied field by the small 20 μm boxes. The gray-scale ranges from 5.94 μT (black) to 6.06 μT (white), By enhancing the gray scale in this image or by applying larger magnetic fields, one could detect the dimagnetic susceptibility of far smaller regions of superconducting material.

Figure 10C:
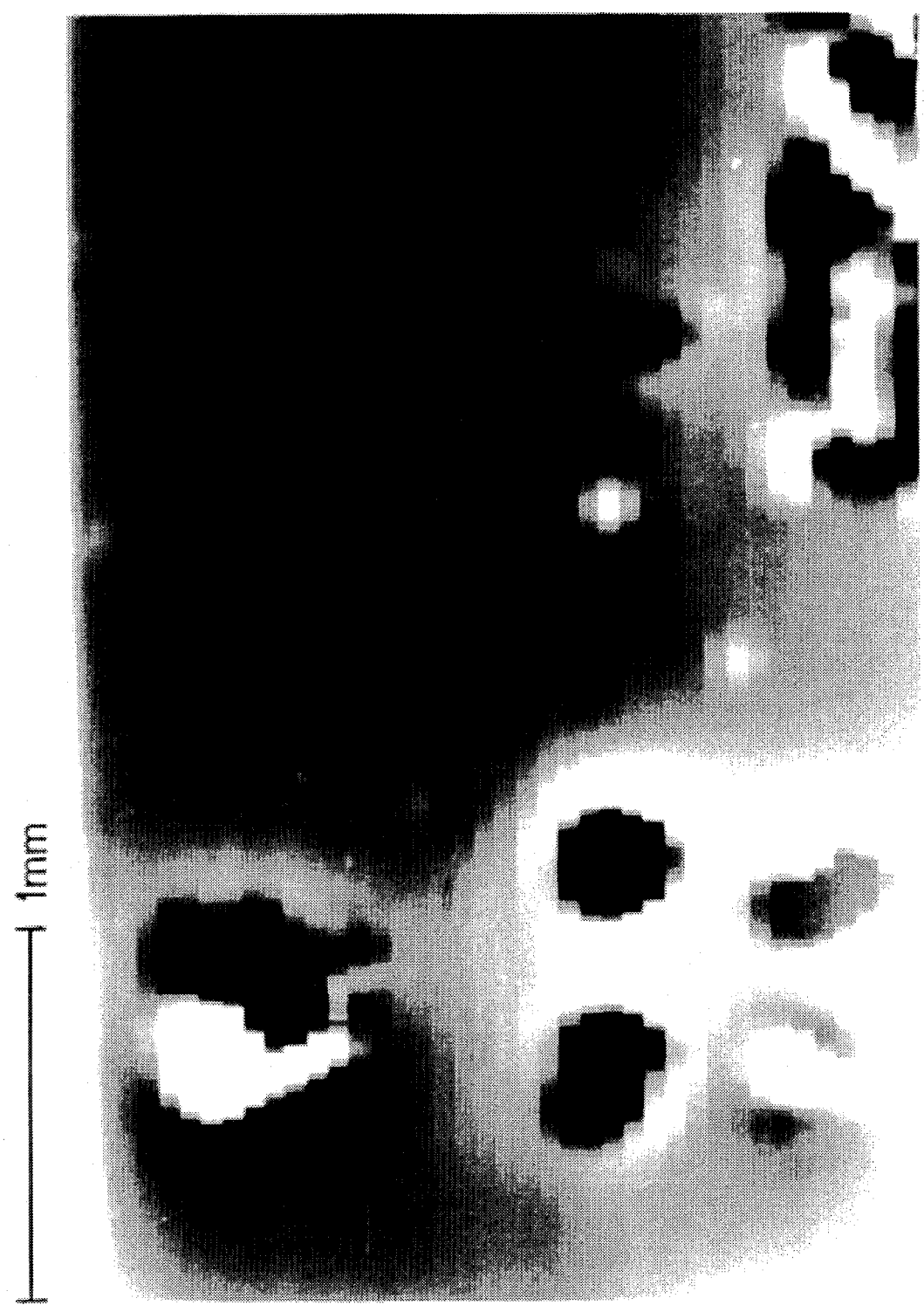
FIG. 10C illustrates the magnetic image of the patterned $YBa_2Cu_3O_7$ sample in zero applied field.

FIG. 10C shows a magnetic image of the same YBCO sample when the applied field is reduced to zero. The remnant fields shown in this image are due to vortices pinned in the superconducting regions or to currents trapped in regions which form closed superconducting loops. From this image, it is apparent that six of the 95 μm wide boxes have flux trapped in them while all the large boxes exhibit some remnant field. From the measured size of the flux coming from the boxes, as well as the fact that only a fraction of the boxes contain flux. It may be concluded that the trapped flux represents individual vortices. In this image, the black and white are corresponding to a difference in $B_z$ of 44 nT.

To determine the field sensitivity of the 3D microscope, the equivalent flux noise spectrum from the flux-locked SQUID 70 is measured using a Hewlett-Packard 35665A dynamic signal analyzer (not shown). The equivalent flux noise ranged from 0.1 to 0.4 m $\phi_o$ Hz$^{-\frac{1}{2}}$ from 1 Hz to 1 kHz. Knowing the effective pickup area of our SQUID 70, a corresponding field sensitivity of 20 to 80 pT Hz$^{-\frac{1}{2}}$ over the same frequency range is measured. These images reveal magnetic details down to about 200 pT.

In conclusion, a magnetic flux microscope which operates at 77K and uses a YBCO SQUID as a magnetic sensor has been constructed. Tests have demonstrated the ability to the obtain images on such common nonconducting substrates as plastic, paper and single crystal insulators. It should be pointed out that the ability to image very small superconducting regions embedded in an otherwise non-superconducting material is potentially very important since it could allow for the identification of new classes of superconducting materials which might otherwise be overlooked in bulk susceptibility measurements. It should be appreciated that improved spatial resolution may be achieved by using a smaller SQUID. Additionally, images as a function of sample temperature may be obtained by placing the sample and SQUID stages in a vacuum.

Finally, it should be appreciated that a plurality of SQUIDS may be placed in an array instead of just utilizing one SQUID.

Although the present invention has been fully described in connection with the preferred embodiment thereof with reference to the accompanying drawings, it to be noted that various changes and modifications are apparent to those skilled in the art. Such changes and modifications are to be understood as included within the scope of the present invention as defined by the appended claims, unless they depart therefrom.

What is claimed is:

1. An apparatus for obtaining microscopic images of magnetic fields emanating from a sample, said sample being an object or specimen which is to be examined by said apparatus, said magnetic fields emanating from said sample, originating from said sample or being induced in said sample by means of an applied magnetic field, said images having a spatial resolution finer than 1 mm and said apparatus comprising:

a dewar;

at least one SQUID contained within said dewar, said SQUID having a loop or body being smaller than 1 mm and disposed within 1 mm of said sample;

a magnetic shield about said dewar;

a positioning assembly at least partially within said dewar and attached to said sample and said at least one SQUID, said sample being disposed in said dewar, and said positioning assembly for moving said sample and said at least one SQUID relative to each other while maintaining said SQUID within at least 1 mm of said sample, and for eliminating vibration which may affect said microscopic images having a spatial resolution finer than 1 mm;

means for controlling the movement of said positioning assembly; and means for monitoring voltage across at least one of said SQUIDs within said dewar to obtain microscopic images of magnetic fields emanating from said sample, said voltage being an output from at least one of said SQUIDs and being generated by at least one of said SOUIDs responding to said magnetic fields emanating from said sample.

2. The apparatus according to claim 1, wherein said sample is attached to a sample holder.

3. The apparatus according to claim 1, further comprising a mounting means for maintaining said at least one SQUID stationary relative to said magnetic shield.

4. The apparatus according to claim 1, wherein at least one of said SQUIDs is a low noise thin film DC SQUID.

5. The apparatus according to claim 1, further comprising a feedback coil which couples feedback flux to at least one of said SQUIDs, and at least one field coil for applying flux to said sample, said feed back coil being disposed in said dewar and proximal to said SQUID.

6. The apparatus according to claim 1, further comprising a feedback coil for applying flux, to said SQUID, from a feedback electronic device which monitors an output of at least one of said SQUIDs, said feed back coil being disposed in said dewar and proximal to said SQUID; at least one field coil for applying flux to said sample said field coil being disposed in said dewar and proximal to said SQUID; and a means for storing, analyzing and displaying data.

7. The apparatus according to claim 1, wherein said means for controlling said positioning assembly and said means for monitoring fields is a computer.

8. The apparatus according to claim 6, wherein said means for storing, analyzing, and displaying further comprises an analog to digital converter in cooperation with at least one of said SQUIDs.

9. The apparatus according to claim 8, wherein said analog to digital converter is coupled to at least one of said SQUIDs and said positioning assembly.

10. The apparatus according to claim 1, wherein said positioning assembly has at least one stepping motor for providing precise linear motion to said sample.

11. The apparatus according to claim 1, wherein said positioning assembly further comprises at least one position transducer.

12. The apparatus according to claim 1, wherein said positioning assembly further comprises vibration isolators.

13. The apparatus according to claim 1, wherein said positioning assembly has components made of non-magnetic materials.

14. The apparatus according to claim 13, wherein said non-magnetic materials comprises non-metallic and metallic components.

15. The apparatus according to claim 14, wherein said non-metallic components are selected from the group consisting of fiberglass and plastics.

16. A method of obtaining images of magnetic fields from a sample, said sample being an object or specimen which is to be examined, said magnetic fields emanating from said sample originating from said sample or being induced in said sample by means of an applied magnetic field, said method comprising the steps of:

placing a sample inside of a dewar;

providing a magnetic shield about said dewar;

moving a positioning assembly, disposed at least partially within said dewar, to position said sample and a SQUID relative to each other within said dewar, said positioning assembly also for maintaining said SQUID within at least 1 mm of said sample and for eliminating vibration which may affect microscopic images having a spatial resolution finer than 1 mm, wherein said SQUID has a loop or body smaller that 1 mm and is disposed within 1 mm of said sample;

controlling the movement of said positioning assembly to vary the relative position between the SQUID and the sample while maintaining said SQUID within at least 1 mm of said sample; and monitoring a voltage across at least one of said SQUIDs within said dewar to obtain microscopic images of magnetic fields emanating from said sample, said voltage being an output from at least one of said SQUIDs and being generated by at least on of said SOUIDs responding to said magnetic fields emanating from said sample; and generating a microscopic image of magnetic fields emanating from said sample, said microscopic image having a spatial resolution finer than 1 mm, by plotting said output from said SQUID as a function of a position of said positioning assembly so as to represent microscopic spacial dependence of any magnetic fields emanating from said sample.

17. A method according to claim 15, further comprising a step of maintaining said SQUID stationary relative to said magnetic shield.

18. A method according to claim 16, further comprising the step of supplying feedback signals to a feedback coil to provide system stability.

19. A method according to claim 16, further comprising the step of modulating a signal to provide a variety of magnetic fields for application to said sample.

20. A method according to claim 19 further comprising the step of using said magnetic fields to measure magnetic susceptibility, electrical conductivity or skin depth of said sample.

21. A method according to claim 16, further comprising the step of applying a flux to said sample so as to measure magnetic susceptibility of, electrical conductivity of, thickness of, or the presence of cracks in said sample.

22. A method according to claim 16, further comprising the steps of performing the operations of monitoring, controlling, analyzing and displaying data provided from said SQUID.

23. A method according to claim 16, further comprising the step of supplying current to an electrically conducting portion of said sample so as to detect pathways in which current flows through said sample, to detect the presence of shorted connections or open connections in said pathways in said sample or to detect the presence of cracks or other electrical inhomogeneities in said sample.

24. The apparatus according to claim 1, wherein a distance between said sample and at least one of said SQUIDs is between 1 μm. and 200 μm.

* * * * *

REEXAMINATION CERTIFICATE (3633rd)
United States Patent [19]
Wellstood et al.

[11] B1 5,491,411
[45] Certificate Issued Sep. 22, 1998

[54] METHOD AND APPARATUS FOR IMAGING MICROSCOPIC SPATIAL VARIATIONS IN SMALL CURRENTS AND MAGNETIC FIELDS

[75] Inventors: Frederick C. Wellstood, College Park; Anna Mathai, University Park; Dian Song, Greenbelt; Randall C. Black, Seabrook, all of Md.

[73] Assignee: University of Maryland at College Park, College Park, Md.

Reexamination Request:
No. 90/004,558, Feb. 21, 1997

Reexamination Certificate for:
Patent No.: 5,491,411
Issued: Feb. 13, 1996
Appl. No.: 61,102
Filed: May 14, 1993

[51] Int. Cl.$^6$ .............. G01R 33/035; G01R 33/12; G01N 27/72
[52] U.S. Cl. .......... 324/248; 324/201; 324/224; 324/235; 324/239; 324/262; 324/750; 505/162; 505/846
[58] Field of Search ................. 324/201, 235, 324/239, 240, 248, 750; 505/162, 846; 235/449

[56] References Cited

U.S. PATENT DOCUMENTS

| | | | |
|---|---|---|---|
| 4,912,408 | 3/1990 | Sawada et al. | 324/248 X |
| 5,166,612 | 11/1992 | Murdock | 324/248 X |
| 5,326,986 | 7/1994 | Miller, Jr. et al. | 324/248 X |
| 5,394,083 | 2/1995 | Jiles | 324/240 X |

OTHER PUBLICATIONS

"One–dimensional magnetic flux microscope based on the dc superconducting quantum interference device," *Appl. Phys. Lett.*, vol. 61, No. 5, Aug. 3, 1992, pp. 598–600.

IBM Technical Disclosure Bulletin, vol. 27, No. 10A, "Integrated Thin–Film Miniature Squid Magnetometer", Mar. 1985.

"A Device for Experimental Observation of Flux Vortices Trapped in Superconducting Thin Films" by Francis Patrick Rogers, Master's Thesis, Massachusetts Institute of Technology, Sep. 1983.

*Primary Examiner*—Gerard R. Strecker

[57] ABSTRACT

A magnetic flux microscope that measures the magnetic field about a sample surface. The apparatus uses a thin-film superconducting quantum interference device (SQUID) as the scanning device. Magnetic shielding is provided about the SQUID and is held stationary relative to the SQUID. The apparatus and method provides a very high magnetic image of the sample with a very high spatial and field resolution.

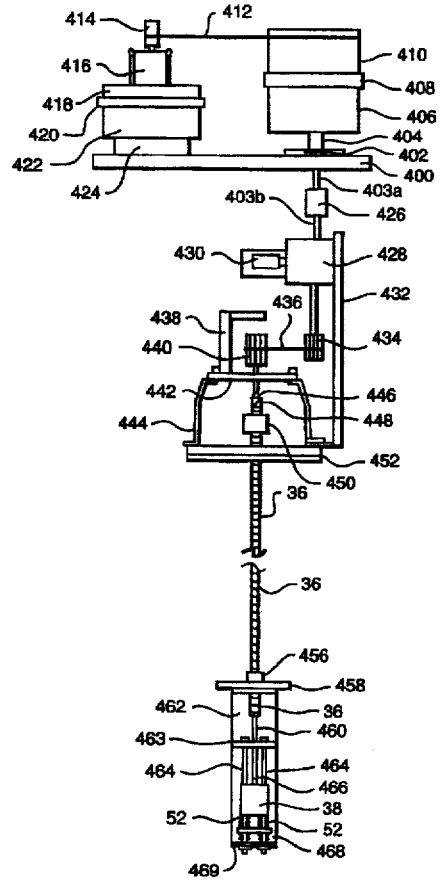

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 9, lines 26–34:

With an applied field of 143 nT, and SQUID 44 positioned at the edge of the 500 μm line, the output voltage varies rapidly with sample 42 position. Dividing the noise at SQUID 44 output by the output-to-position transfer function, a position resolution of 0.5 [mm] *nm* $Hz^{-1/2}$ at 4 Hz was found. This equivalent motional noise is equal to the smallest sample position change which the system can detect in a unit bandwidth for this applied field, and is an upper bound on the relative motion between the sample and SQUID.

AS A RESULT OF REEXAMINATION, IT HAS BEEN DETERMINED THAT:

Claims 1, 16 and 17 are determined to be patentable as amended.

Claims 2–15 and 18–24, dependent on an amended claim, are determined to be patentable.

New claims 25–52 are added and determined to be patentable.

1. An apparatus for obtaining microscopic images of magnetic fields emanating from a sample, said sample being an object or specimen which is to be examined by said apparatus, said magnetic fields emanating from said sample, originating from said sample or being induced in said sample by means of an applied magnetic field, said images having a spatial resolution finer than 1 mm and said apparatus comprising:

a dewar;

at least one *bare* SQUID contained within said dewar, said *bare* SQUID having a loop or body being smaller than 1 mm and disposed within 1 mm of said sample;

a magnetic shield about said dewar;

a positioning assembly at least partially within said dewar and attached to said sample and said at least one *bare* SQUID, said sample being disposed in said dewar, and said positioning assembly for moving said sample and said at least one *bare* SQUID relative to each other while maintaining said *bare* SQUID *loop or body* within at least 1 mm of said sample, and for eliminating vibration which may affect said microscopic images having a spatial resolution finer than 1 mm;

means for controlling the movement of said positioning assembly; and means for monitoring voltage across at least one of said *bare* SQUIDs within said dewar to obtain microscopic images of magnetic fields emanating from said sample, said voltage being an output from at least one of said *bare* SQUIDs and being generated by at least one of said *bare* SQUIDs responding to said magnetic fields emanating from said sample.

16. A method of obtaining images of magnetic fields from a sample, said sample being an object or specimen which is to be examined, said magnetic fields emanating from said sample originating from said sample or being induced in said sample by means of an applied magnetic field, said method comprising the steps of:

placing a sample inside of a dewar;

providing a magnetic shield about said dewar;

moving a positioning assembly, disposed at least partially within said dewar, to position said sample and a *bare* SQUID relative to each other within said dewar, *said bare SQUID having a loop or body*, said positioning assembly also for maintaining said *bare* SQUID *loop or body* within at least 1 mm of said sample and for eliminating vibration which may affect microscopic images having a spatial resolution finer than 1 mm, wherein said *bare* SQUID [has a] loop or body *is* smaller [that] *than* 1 mm and is disposed within 1 mm of said sample;

controlling the movement of said positioning assembly to vary the relative position between the *bare* SQUID and the sample while maintaining said *bare* SQUID *loop or body* within at least 1 mm of said sample; and monitoring a voltage across at least one of said *bare* SQUIDs within said dewar to obtain microscopic images of magnetic fields emanating from said sample, said voltage being an output from at least one of said *bare* SQUIDs and being generated by at least [on] *one* of said *bare* SQUIDs responding to said magnetic fields emanating from said sample; and generating a microscopic image of magnetic fields emanating from said sample, said microscopic image having a spatial resolution finer than 1 mm, by plotting said output from said *bare* SQUID as a function of a position of said positioning assembly so as to represent microscopic spacial dependence of any magnetic fields emanating from said sample.

17. A method according to claim [15] *16*, further comprising a step of maintaining said SQUID stationary relative to said magnetic shield.

*25. An apparatus according to claim 1, wherein said SQUID is a directly coupled magnetometer.*

*26. A method according to claim 16, wherein said voltage is generated by operating said SQUID as a directly coupled magnetometer.*

*27. An apparatus according to claim 10, wherein said positioning assembly further comprises a pushrod, a means for transmitting motion from the stepper motor to the pushrod, a slider, and a holder for the sample, said holder being attached to the slider, said pushrod functionally contacting said slider.*

*28. An apparatus according to claim 25, wherein said means for transmitting motion comprises a cylindrical vibration isolation mass which is functionally driven by said stepper motor.*

*29. An apparatus according to claim 1, wherein said positioning assembly comprises a first pushrod and a second pushrod, wherein said pushrods are capable of moving said sample and said at least one SQUID relative to each other along two orthogonal axes.*

*30. An apparatus according to claim 27, wherein said positioning assembly comprises two stepper motors and two pushrods wherein each motor functionally drives a respective said pushrod.*

*31. An apparatus according to claim 27, wherein said positioning assembly further comprises a means for adjust-* ing a separation distance between the sample and SQUID, which is orthogonal to said axes.

32. An apparatus according to claim 31, wherein said positioning assembly is a means for adjusting, at cryogenic temperature, movement of said SQUID relative to said sample along said axes and said separation distance.

33. An apparatus according to claim 29, wherein said first pushrod is parallel to said second pushrod, wherein said positioning assembly further comprises a third pushrod parallel to said first pushrod and functionally attached to a wedge for adjusting a separation distance between the sample and SQUID, the separation distance being orthogonal to said axes.

34. An apparatus according to claim 1, wherein said microscopic images have a spatial resolution as fine as 50 µm, wherein said SQUID positioning means eliminates vibration which may affect said microscopic images having a spatial resolution as fine as 50 µm.

35. An apparatus according to claim 1, wherein said SQUID positioning means eliminates vibration such that said microscope is capable of microscopic images having a spatial resolution of 50 µm.

36. An apparatus according to claim 1, wherein said microscope is capable of resolving microscopic images of features having a dimension as low as 50 µm.

37. An apparatus according to claim 36, wherein said microscope is capable of discerning magnetic features as small as 20 pico Tesla.

38. An apparatus according to claim 1, wherein said microscope is capable of resolving microscopic images of features having a dimension of 50 µm.

39. An apparatus according to claim 38, wherein said microscope is capable of discerning magnetic features of 20 pico Tesla with a one second averaging time.

40. A method according to claim 16, wherein said moving of said positioning assembly comprises transmitting motion from a stepper motor to a pushrod, a slider, and a holder for the sample, said holder being attached to the slider, said pushrod functionally contacting said slider.

41. A method according to claim 40, wherein eliminating said vibration comprises employing a cylindrical vibration isolation mass which is functionally driven by said stepper motor.

42. A method according to claim 16, wherein said moving of said positioning assembly comprises moving a first pushrod and a second pushrod to move said sample and said at least one SQUID relative to each other along two orthogonal axes.

43. A method according to claim 42, wherein said moving of said positioning assembly comprises having two stepper motors, wherein each stepper motor functionally drives a respective said pushrod.

44. A method according to claim 42, wherein said moving of said positioning assembly further comprises adjusting a separation distance between the sample and SQUID, which is orthogonal to said axes.

45. A method according to claim 44, wherein said moving of said positioning assembly to move said SQUID relative to said sample occurs at cryogenic temperature along said axes and said separation distance.

46. A method of claim 42, wherein said first pushrod is parallel to said second pushrod, wherein said moving of said positioning assembly further comprises moving a third pushrod parallel to said first pushrod and functionally attached to a wedge to adjust a separation distance between the sample and SQUID, the separation distance being orthogonal to said axes.

47. A method according to claim 16, wherein said microscopic images have a spatial resolution as fine as 50 µm, and said SQUID positioning assembly eliminates vibration which may affect said microscopic images having a spatial resolution as fine as 50 µm.

48. A method according to claim 16, wherein said SQUID positioning assembly eliminates vibration such that said microscope is capable of microscopic images having a spatial resolution of 50 µm.

49. A method according to claim 16, wherein said microscope resolves microscopic images of features having a dimension as low as 50 µm.

50. A method according to claim 49, wherein said microscope discerns magnetic features as small as 20 pico Tesla.

51. A method according to claim 16, wherein said microscope resolves microscopic images of features having a dimension of 50 µm.

52. A method according to claim 51, wherein said microscope discerns magnetic features of 20 pico Tesla with a one second averaging time.

* * * * *